United States Patent

Bös et al.

Patent Number: 5,990,105
Date of Patent: Nov. 23, 1999

[54] BENZOSULFONE DERIVATIVES

[75] Inventors: Michael Bös, Rheinfelden; Walter Hunkeler, Magden, both of Switzerland; Claus Riemer, Freiburg, Germany

[73] Assignee: Hoffmann-La Roche Inc., Nutley, N.J.

[21] Appl. No.: 09/232,775

[22] Filed: Jan. 15, 1999

[30] Foreign Application Priority Data

Jan. 16, 1998 [EP] European Pat. Off. ............ 98100690

[51] Int. Cl.$^6$ ............ A61K 35/535; C07D 413/00; C07D 207/00; C07C 315/00
[52] U.S. Cl. ............ 514/235.5; 514/235.8; 514/269; 514/318; 514/421; 544/122; 544/124; 544/158; 544/319; 548/523; 568/30; 568/33
[58] Field of Search ............ 514/235.5, 235.8, 514/269, 318, 429; 544/122, 124, 158, 319, 360; 548/523; 568/30, 33

[56] References Cited

FOREIGN PATENT DOCUMENTS 524 781 7/1992 European Pat. Off. .
09059254 3/1997 Japan .

OTHER PUBLICATIONS

H. Yamanaka, S. Ogawa and S. Konno, *Chem. Pharm. Bull.*, 29, pp. 98–104, 1981.

R. Gerdil, *Helvetica Chimica Acta*, 56, pp. 196–206, 1973.

B.L. Roth, S.C. Craigo, M.S. Choudhary, A. Uluer, F.J. Monsma Jr., Y. Shen, H.Y. Meltzer and D. R. Sibley, *J. Pharmacol. & Exp. Ther.*, 268, pp. 1403–1410, 1994.

F.J. Monsma, Jr., Y. Shen, R.P. Ward, M.W. Hamblin and D.R. Sibley, *Mol. Pharmacol.*, pp. 320–327, 1993.

A. Bourson, E. Borroni, R.H. Austin, F.J. Monsma Jr. and A.J. Sleight, *J. Mol. Pharmacol. & Exp. Ther.*, 274, pp. 173–180, 1995.

R.P. Ward, M.W. Hamblin, J.E. Lachowicz, B.J. Hoffman, D.R. Sibley and D.M. Dorsa, *Neuroscience*, 64, pp. 1105–1111, 1995.

A.J. Sleight, F.G. Boess, A. Bourson, D.R. Sibley and F.J. Monsma Jr., *Neurotransmissions*, 11, pp. 1–5, 1995.

Abstract of Japanest Patent No. 09059254.

W. Klotzer, *Monatshefte Chemie*, 92, pp. 1212–1217 (1961).

*Primary Examiner*—Johann Richter
*Assistant Examiner*—Joseph Murray
*Attorney, Agent, or Firm*—George W. Johnston; Dennis P. Tramaloni; Joseph P. Kirk, Jr.

[57] ABSTRACT

The present invention relates to novel compounds of the general formula

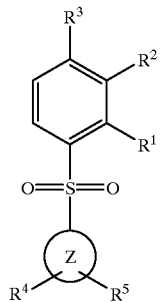

I wherein
$R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—;
Z is pyrimidin-4-yl, pyridin-4-yl, pyridin-2-yl or phenyl;
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH$(CH_2)_n$NR$^6$R$^7$, —N$(CH_3)(CH_2)_n$NR$^6$R$^7$, —NH$(CH_2)_n$-morpholin-4-yl or —NH$(CH_2)_n$OH;
n is 2–4
$R^6$ and $R^7$ are each independently hydrogen or lower alkyl, and to their pharmaceutically acceptable salts.

It has been found that the compounds of formula I possess a selective affinity to 5HT-6 receptors.

29 Claims, No Drawings

BENZOSULFONE DERIVATIVES

INTRODUCTION

The present invention relates to novel compounds of the general formula I

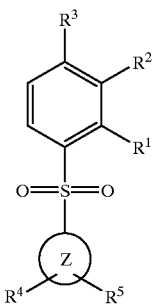

I wherein $R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—;
Z is pyrimidin-4-yl, pyridin-4-yl, pyridin-2-yl or phenyl;
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;
n is 2,3 or 4
$R^6$ and $R^7$ are each independently hydrogen or lower alkyl,
and to their pharmaceutically acceptable salts
providing however, that
when Z is pyrimidin-4-yl, $R^4$ is different from $R^5$,
when Z is pyridin-2-yl, $R^5$ is not lower alkyl and
when Z is phenyl, $R^4$ and one of $R^1$–$R^3$ are different from hydrogen.

Compounds, which have been disclaimed from the present invention are described in Monatshefte Chemie, 92, 1212, (1961), Chem. Pharm. Bull., 29(1), 98–104, (1981), JP 09059254, EP 524781 and Helv. Chim. Acta, 56(1), 196–206, (1973).

SUMMARY

The invention comprises compounds of the structures set forth below and methods of treatment or prevention of phychoses, schizophrenia, manic depressions, depressions, neurological disorders, memory disorders, Parkinson's disease, amyotrophic lateral sclerosis, Alzheimer's disease and Huntington's disease.

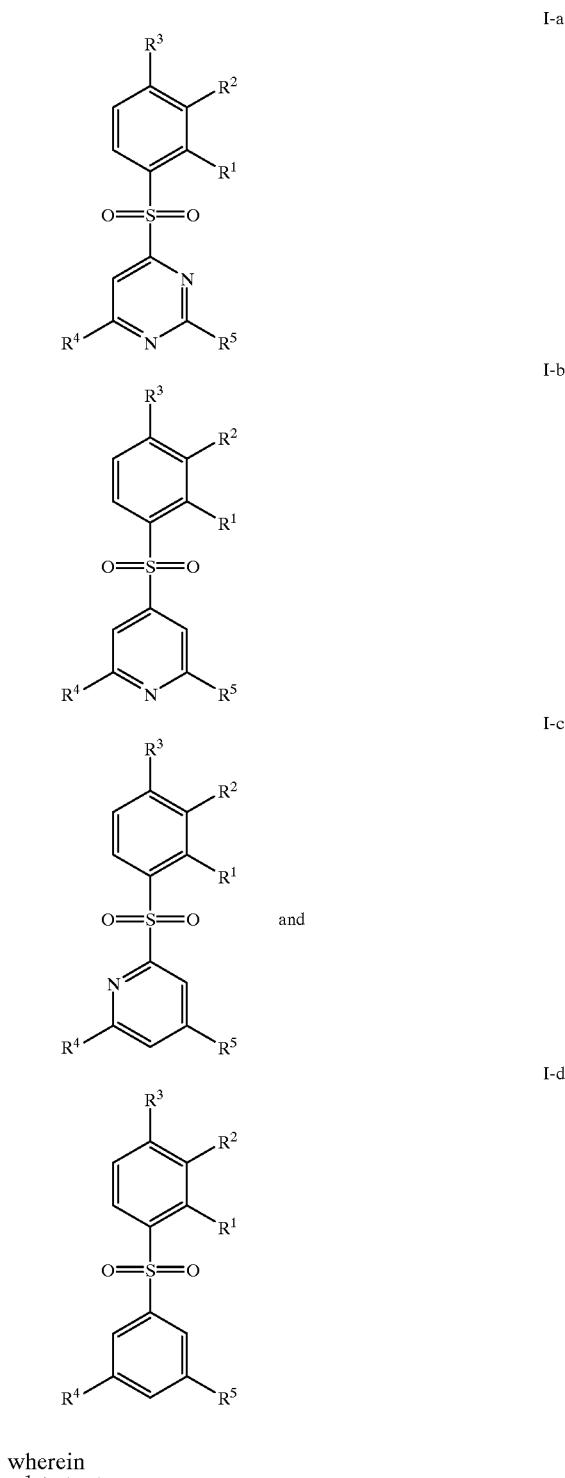

wherein
$R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—;
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH2)$_n$-morpholin-4-yl or —NH(CH$_2$)$_n$OH;

n is 2, 3 or 4.

The following compounds of formulae I-a, I-b, I-c and I-d are especially preferred for the above-mentioned use:

[4-(4-amino-benzenesulphonyl)-6-bromopyrimidine-2-yl]-methylamine in accordance with formula I-a,
[4-(4-amino-benzenesulphonyl)-6-bromopyridine-2-yl]-methylamine,
[4-(4-amino-benzenesulphonyl)-6-bromopyridine-2-yl]-dimethylamine,
4-(2-chloro-6-pyrrolidine-1-yl-pyridine-4-sulfonyl)-phenylamine,
4-(2-bromo-6-pyrrolidine-1-yl-pyridine-4-sulphonyl)-phenylamine,
4-(2-iodo-6-pyrrolidine-1-yl-pyridine-4-sulphonyl)-phenylamine,
4-(2-bromo-6-piperazin-1-yl-pyridine-4-sulphonyl)-phenylamine,
4-(2-phenyl-6-pyrrolidine-1-yl-pyridine-4-sulphonyl)-phenylamine,
N-[4-(4-amino-benzenesulfonyl)-6-bromopyridine-2-yl]-N', N'-dimethylethan-1,2-diamine,
N-[4-(4-amino benzenesulphonyl)-6-bromopyridine-2-yl]N, N',N'-trimethyl-ethan-1,2-diamine,
N-[4-(4-amino-benzenesulphonyl)-6-bromopyridine-2-yl]-N',N'-dimethyl-propane-1,3-diamine,
N-[4-(4-amino-benzenesulphonyl)-6-bromopyridine-2-yl]-N',N'-diethyl-propane-1,3-diamine,
N1-[4-(4-amino-benzenesulphonyl)-6-bromopyridine-2-yl]-butan-1,4-diamine and
1-[6-bromo-4-(3-trifluoromethyl-benzenesulphonyl)-pyridine-2-yl]piperazin in accordance with formula I-b,
[2-(4-amino-benzenesulphonyl )-6-bromopyridine-4-yl]-methylamine in accordance with formula I-c
and
4-(3,5-dimethoxy-benzenesulphonyl)-phenylamine,
[3-(4-amino-benzenesulphonyl)-5-bromophenyl]-methylamine,
[3-(4-amino-phenylsulphonyl)-5-bromophenyl]-dimethylamine,
[3-(4-amino-benzenesulphonyl)-5-bromophenyl]-ethylmethylamine,
4-[3,5-dimethoxybenzenesulphonyl)-2-methylphenylamine,
N-[3-(4-amino-benzenesulphonyl)-5-bromophenyl]-N'-methylpropane-1,3-diamine and
3-[3-(4-amino-benzenesulphonyl)-5-bromophenylamino]-propan-1-ol in accordance with formula I-d.

DETAILED DESCRIPTION

Surprisingly, it has been found that the compounds of formula I of the present invention possess a selective affinity to 5HT-6 receptors. The neurotransmitter 5-hydroxytryptamine (5HT) is a major modulatory neurotransmitter in the brain and its effects are mediated by a family of receptors which, according to our present knowledge, is comprised of 13 G-protein coupled receptors and one ligand-gated ion channel. The 5HT-6 receptor was identified using molecular biological techniques without prior knowledge of its physiological function or pharmacology. Subsequently, a number of different techniques have been used to identify the function of the 5HT-6 receptor, including experiments with antisense oligonucleotides, transgenic animals and, of course, the identification of selective antagonists for the receptor using classical medicinal chemistry approaches. It has been shown that the 5HT-6 receptor appears to be almost exclusively present in the brain with little evidence for its presence in peripheral tissues. Based on a hight level of 5HT-6 receptor mRNA in the hippocampus, it has been stated that the 5HT-6 receptor play a role in the pathology and treatment of depression and/or affective disorders. They are accordingly suitable for the treatment or prevention of central nervous disorders such as, for example, psychoses, schizophrenia, manic depressions (Bryan L. Roth et al., J. Pharmacol. Exp. Ther., 268, pages 1403–1410 (1994)), depressions (David R. Sibley et al., Mol. Pharmacol., 43, pages 320–327 (1993)), neurological disorders (Anne Bourson et al., J. Pharmacol. Exp. Ther., 274, pages 173–180 (1995); R. P. Ward et al., Neuroscience, 64, pages 1105–1110 (1995)), memory disorders, Parkinson's disease, amyotrophic lateral sclerosis, Alzheimer's disease and Huntington's disease (Andrew J. Sleight et al., Neurotransmissions, 11, pages 1–5 (1995)).

Objects of the present invention are compounds of formula I and pharmaceutically acceptable addition salts thereof, the preparation of the above-mentioned compounds, medicaments containing them and their manufacture as well as the use of the above-mentioned compounds in the control or prevention of illnesses, especially of illnesses and disorders of the kind referred to earlier, or for the manufacture of corresponding medicaments.

The term "lower alkyl" used in the present description denotes residues of 1 to 7, preferably of 1 to 4, carbon atoms, such as, for example, methyl, ethyl, n-propyl, i-propyl, n-butyl, i-butyl and t-butyl.

The term "lower alkoxy" denotes a lower alkyloxy residue wherein lower alkyl is as defined above, such as, for example, methoxy, ethoxy, n-propoxy, i-propoxy, n-butoxy, i-butoxy and t-butoxy.

The term "lower alkylamino" denotes a group wherein the lower alkyl residue is as defined above, such as, for example, methylamino and ethylamino.

The term "di-lower alkylamino" denotes a group with two identical or different lower alkyl residues as defined above, such as, for example, dimethylamino, diethylamino or methyl-ethyl-amino.

The term "amino protecting group" means a protecting group that preserves a reactive amino group that otherwise would be modified by certain chemical reactions. These groups are well known in the art. Preferred in the present invention are the acetyl group and the BOC group.

The term "pharmaceutically acceptable salts" embraces salts with inorganic and organic acids such as hydrochloric acid, hydrobromic acid, nitric acid, sulphuric acid, phosphoric acid, citric acid, formic acid, fumaric acid, maleic acid, acetic acid, succinic acid, tartaric acid, methanesulphonic acid, p-toluene-sulphonic acid and the like as well as salts with inorganic bases such as sodium or potassium hydroxide. Such salts can be manufactured readily by any person skilled in the art having regard to the state of the art and taking into consideration the nature of the compound to be converted into a salt.

The compounds of formula I and their salts can be manufactured in a manner, known per se, which process comprises a) converting a corresponding nitro compound into an amino compound of formula I, or b) oxydizing the sulfanyl group in a compound of formula II

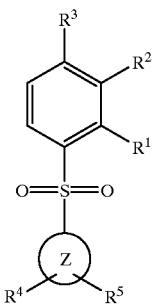

into a sulfonyl group,
wherein
R$^1$ is hydrogen;
R$^2$ is hydrogen, trifluoromethyl or lower alkyl;
R$^3$ is hydrogen or amino; or
R$^1$ and R$^2$ or R$^3$ and R$^2$ taken together are —CH=CH—CH=CH—;
Z is pyrimidin-4-yl, pyridin-4-yl, pyridin-2-yl or phenyl;
R$^4$, R$^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, C$_3$–C$_6$ cycloalkyl, C$_3$–C$_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;
n is 2, 3 or 4
, or
c) reacting a compound of formula III

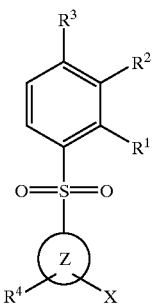

wherein
R$^1$ is hydrogen;
R$^2$ is hydrogen, trifluoromethyl or lower alkyl;
R$^3$ is hydrogen or amino; or
R$^1$ and R$^2$ or R$^3$ and R$^2$ taken together are —CH=CH—CH=CH—;
R$^4$ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, C$_3$–C$_6$ cycloalkyl, C$_3$–C$_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;
n is 2, 3 or 4;

Z is pyridyl or pyrimidyl and X is halogen or nitro, with a compound of formula

HNR'R"

wherein R' and R" each independently are hydrogen, lower alkyl, —(CH$_2$)$_n$NR$^6$R$^7$, —(CH$_2$)$_n$-morpholin-4-yl or —(CH$_2$)$_n$OH, or R', R" taken together with the N-atom to which they are attached are —(CH$_2$)$_2$N(CH$_2$)$_2$, —(CH$_2$)$_2$O(CH$_2$)$_2$- or —(CH$_2$)$_4$— to a compound of formula I, wherein R$^5$ is amino, lower alkyl-amino, di-lower alkyl-amino, piperazinyl, morpholinyl, pyrrolidinyl, —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH, n is 2–4 and R$^6$ and R$^7$ are hydrogen or lower alkyl, or
d) alkylating a corresponding amino group of a compound of formula I into a lower alkyl-amino group or a di-lower alkyl-amino group, or
e) cleaving off an amino protecting group in a compound of formula IV

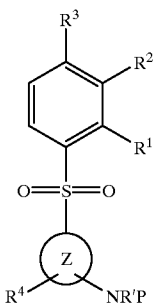

wherein
R$^1$ is hydrogen;
R$^2$ is hydrogen, trifluoromethyl or lower alkyl;
R$^3$ is hydrogen or amino; or
R$^1$ and R$^2$ or R$^3$ and R$^2$ taken together are —CH=CH—CH=CH—;
Z is pyrimidin-4-yl, pyridin-4-yl, pyridin-2-yl or phenyl;
R$^4$ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, C$_3$–C$_6$ cycloalkyl, C$_3$–C$_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;
n is 2, 3 or 4
R' is hydrogen, lower alkyl, —(CH$_2$),NR$^6$R$^7$, —(CH$_2$)$_n$-morpholin-4-yl or —(CH$_2$)$_n$OH, or R', R" taken together with the N-atom to which they are attached are —(CH$_2$)$_2$N(CH$_2$)$_2$, —(CH$_2$)$_2$O(CH$_2$)$_2$— or —(CH$_2$)$_4$— to a compound of formula I, wherein R$^5$ is amino, lower alkyl-amino, di-lower alkyl-amino, piperazinyl, morpholinyl, pyrrolidinyl, —NH(CH$_2$)$_n$NR$^6$R$^7$, —N(CH$_3$)(CH$_2$)$_n$NR$^6$R$^7$, —NH(CH$_2$),-morpholin-4-yl or —NH(CH$_2$)$_n$OH, n is 2–4 and R$^6$ and R$^7$ are hydrogen or lower alkyl, and P is an amino protecting group, or
f) modifying the substituents R$^4$ or R$^5$ or both within the definition given above and
if desired, converting a compound of formula I into a pharmaceutically acceptable salt.

In accordance with process variant a) a nitro group in a compound of formula II is converted into a corresponding amino group. This method is known in the art and may be carried out with a reducing agent, such as Fe powder in the presence of $NH_4Cl$ and, preferably, in a mixture of solvents, for example, methanol/dioxane (1:1).

This reaction is described, for example in more detail in the working examples 2, 8, 56, 57 and 69.

A further method is the reduction in a $H_2$ atmosphere in the presence of a catalyst, such as Pd/C, at room temperature, described, for example, in working examples 61 and 65.

The oxydation of a sulfanyl group, described in process variant b) is carried out in conventional manner, for example by reaction with an oxydizing agent, such as $NaIO_4$ or with m-chlorperbenzene carboxylic acid, described in more detail in examples 1 and 2.

The amination in accordance with variant c) is carried out with a suitable amine, such as methylamine, (example 9), dimethylamine (example 10), pyrrolidine (example 12), piperazine (example 40), morpholine (example 41), 2-dimethylaminoethylamine (example 42), trimethylethylendiamine (example 43), 4-(3-aminopropyl)-morpholine (example 44), 3-methylaminopropylamine (example 45), 3-dimethylamino-1-propylamine (example 46), 3-diethylamino-1-propylamine (example 47), 3-amino-1-propanol (example 48) or N-tert.-butoxycarbonyl-1,4-diaminobutan (example 49) in dioxane or ethanol at a temperature of about 20–50 ° c.

The alkylation of an amino group into a mono- or di-substituted alkyl amino group is conveniently carried out as follows:

A compound of formula I, which contains an amino group is dissolved in acetonitrile and treated with e.g. formaldehyde and $NaBH_3CN$. After adjusting to pH 6 using, for example, glacial acetic acid, this procedure is repeated with a methylamino compound of formula I being obtained after a reaction period of about 2 hours. Another method comprises treating a compound of formula I which contains an amino group with, for example, formic acid and subsequently hydrogenating in a $BH_3$—THF solution.

Suitable protecting groups and methods for their cleavage will be familiar to any person skilled in the art, although of course there can be used only those protecting groups which can be cleaved off by methods under conditions of which other structural elements in the compounds are not affected, such as the acetyl group or the BOC group. The acetyl group in a compound of formula VII may be cleaved off by reaction with a mixture of dioxane and NaOH by heating under reflux. This reaction is described in more detail in example 67. In example 49 is described the cleavage of the BOC group.

Examples in accordance with variant f), wherein $R^4$ and/or $R^5$ may be modified within the definitions given above, are the following:
  replacement of a halogen atom by another one (example 7),
  replacement of a halogen atom, preferrably bromo, by the following groups: vinyl (example 15), t-butylethinyl (example 21), hydroxyalkylethinyl (example 22), phenylethinyl (example 23), cycloalkenyl (example 19) or by unsubstituted or substituted phenyl (examples 24–34 and 38),
  hydrogenation of an lower alkenyl group (examples 16 and 17).

These reactions are familiar to any person skilled in the art.

The salt formation in accordance with variant is effected according to methods which are generally usual and which will be familiar to any person skilled in the art. The basic compounds of formula I can be converted into pharmaceutically acceptable salts, for example with hydrogen chloride, hydrogen bromide, phosphoric acid, sulfonic acid, citric acid, p-toluenesulfonic acid and the like.

The following schemes 1–9 illustrate processes for the preparation of compounds of formula I in more detail. These reactions are familiar to any person skilled in the art.

The starting materials required for the manufacture of the compounds of formula I are known compounds or can be prepared from known compounds by well known processes.

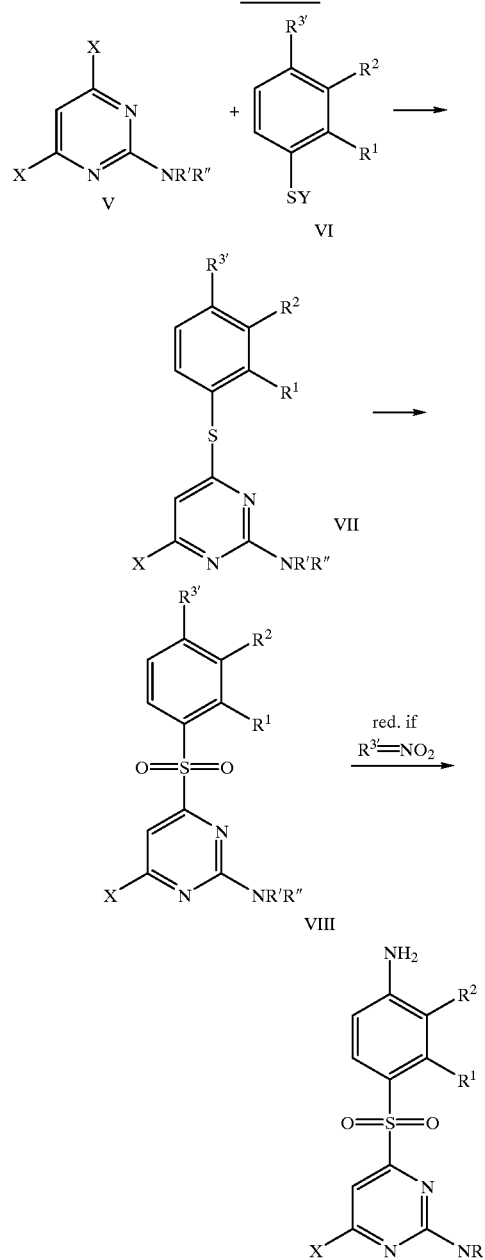

Scheme 1 wherein
$R^1$ is hydrogen;
$R^2$ is hydrogen, trifluoromethyl or lower alkyl; or
$R^1$ and $R^2$ taken together are —CH=CH—CH=CH—;

R' and R" each independently are hydrogen, lower alkyl, —(CH$_2$)$_n$NR$^6$R$^7$, —(CH$_2$)$_n$-morpholin-4-yl or —(CH$_2$)$_n$OH, or R', R" taken together with the N-atom to which they are attached are —(CH$_2$)$_2$N(CH$_2$)$_2$, —(CH$_2$)$_2$O(CH$_2$)$_2$— or —(CH$_2$)$_4$— to a compound of formula I, wherein R$^5$ is amino, lower alkyl-amino, di-lower alkyl-amino, piperazinyl, morpholinyl, pyrrolidinyl, —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH, n is 2–4 and R$^6$ and R$^7$ are hydrogen or lower alkyl, Y is an alkali metal, such as Na or K, X is halogen and R$^{3'}$ is hydrogen or nitro.

Scheme 2

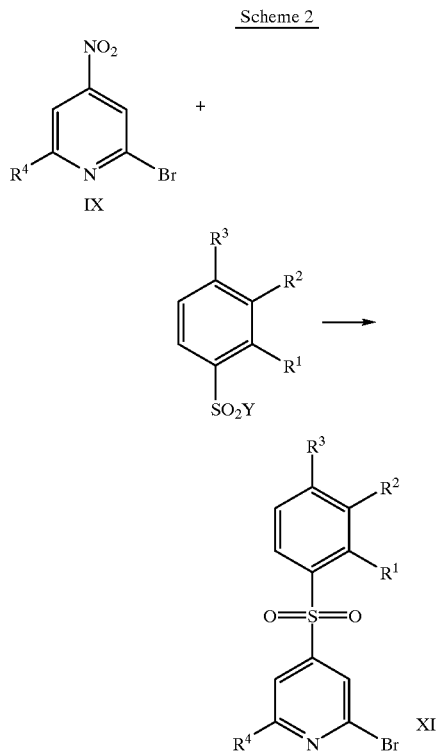

wherein

R$^1$ is hydrogen;

R$^2$ is hydrogen, trifluoromethyl or lower alkyl;

R$^3$ is hydrogen or amino; or

R$^1$ and R$^2$ or R$^3$ and R$^2$ taken together are —CH=CH—CH=CH—;

R$^4$ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, C$_3$–C$_6$ cycloalkyl, C$_3$–C$_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;

n is 2, 3 or 4;

Y is an alkali metal, such as Na or K.

Scheme 3

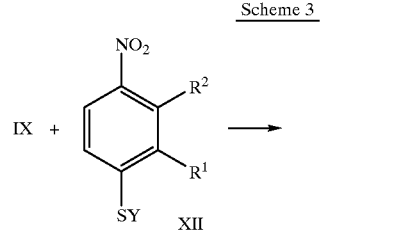

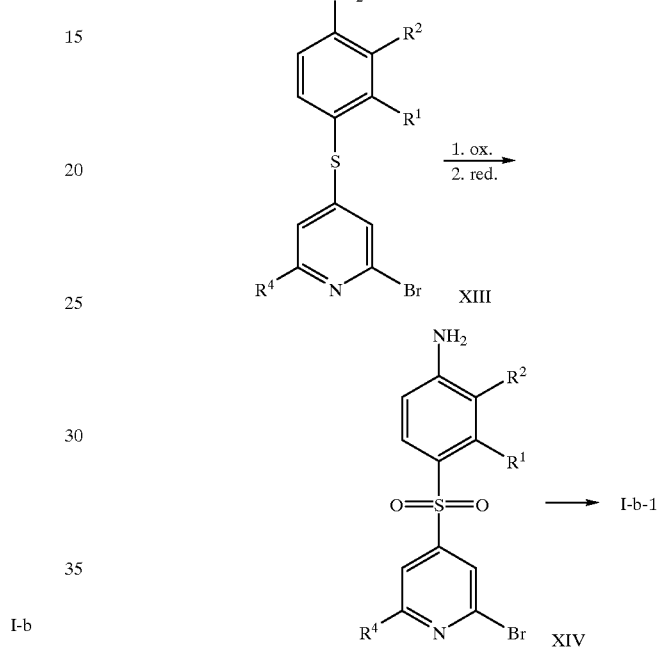

wherein

R$^1$ is hydrogen;

R$^2$ is hydrogen, trifluoromethyl or lower alkyl; or

R$^1$ and R$^2$ taken together are —CH=CH—CH=CH—;

R$^4$ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, C$_3$–C$_6$ cycloalkyl, C$_3$–C$_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;

n is 2, 3 or 4;

Y is an alkali metal, such as Na or K.

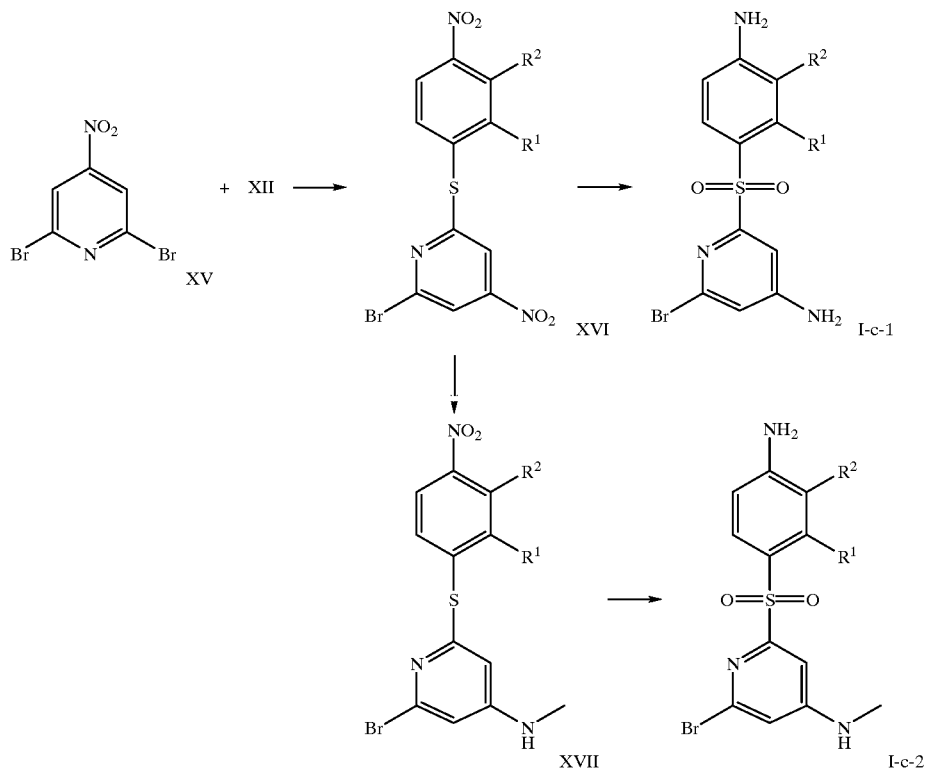
Scheme 4
wherein
$R^1$ is hydrogen;
$R^2$ is hydrogen, trifluoromethyl or lower alkyl; or
$R^1$ and $R^2$ taken together are —CH=CH—CH=CH—;
and Y in XII is an alkali metal.
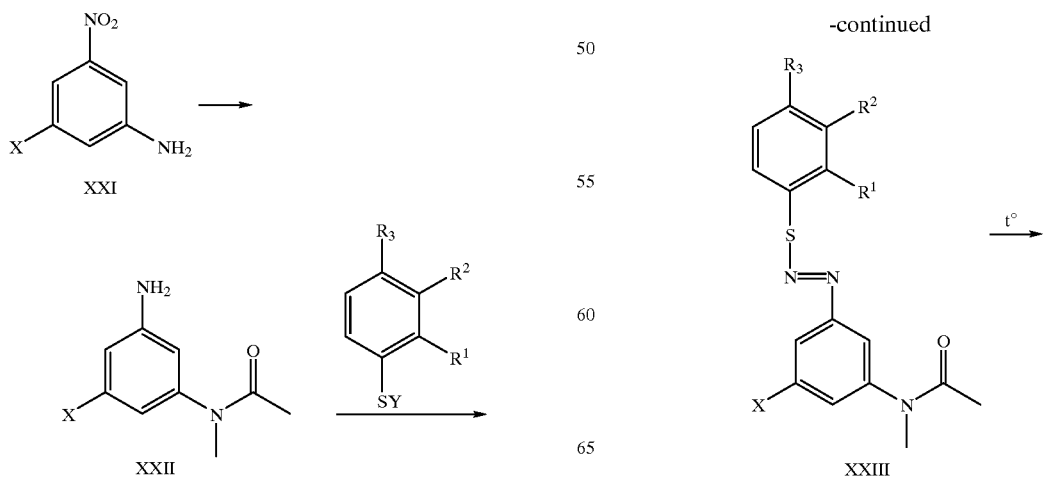
Scheme 5

-continued
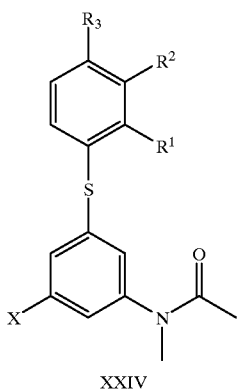
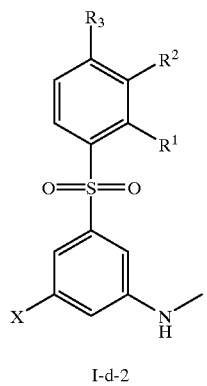
wherein
R¹ is hydrogen;
R² is hydrogen, trifluoromethyl or lower alkyl; or
R¹ and R² taken together are —CH=CH—CH=CH—;
Y is an alkali metal, such as Na or K;
X is halogen; and
R³ is hydrogen.
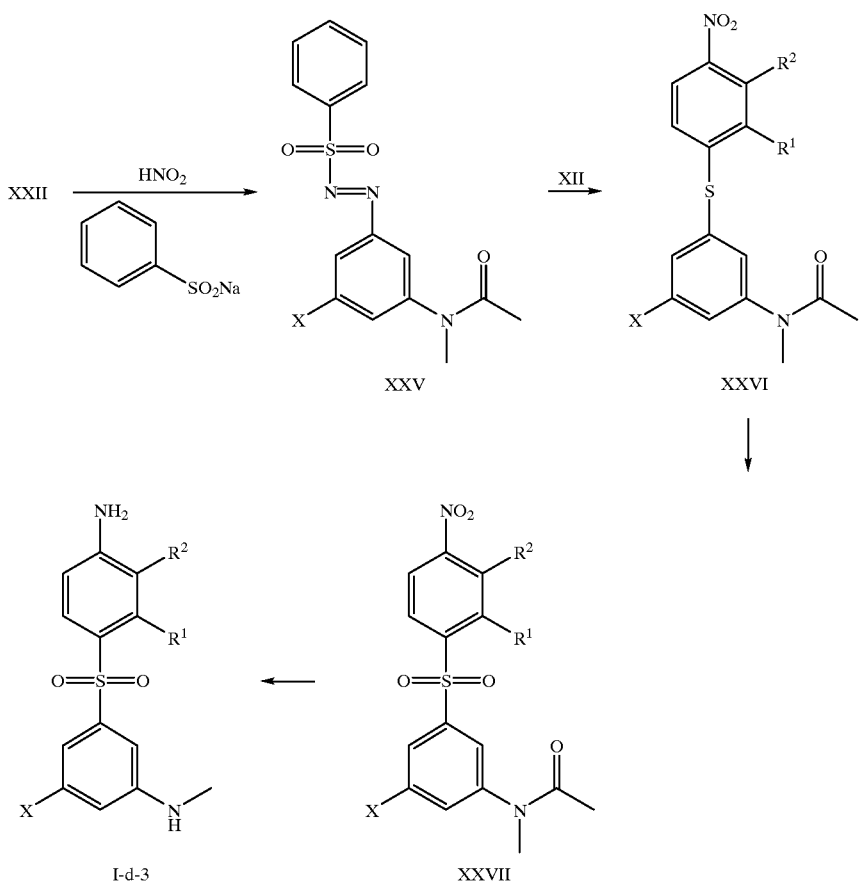
wherein
R¹ is hydrogen;
R² is hydrogen, trifluoromethyl or lower alkyl; or
R¹ and R² taken together are —CH=CH—CH=CH—; and
X is halogen.

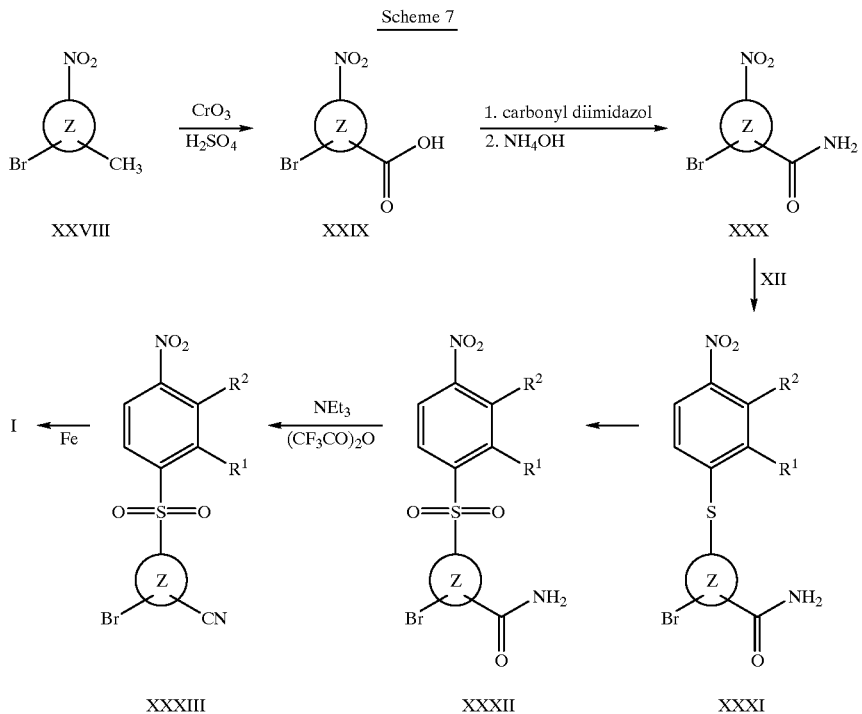

wherein $R^1$ is hydrogen;
$R^2$ is hydrogen, trifluoromethyl or lower alkyl; or
$R^1$ and $R^2$ taken together are —CH=CH—CH=CH—; and
Z is pyridyl-4yl.

Scheme 8

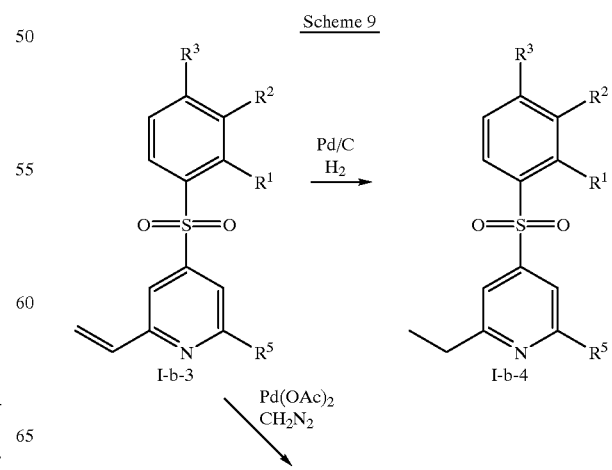

wherein $R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—;
$R^5$ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3C_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$NR$^6$R$^7$, —NH(CH$_2$)$_n$-morpholin-4-yl or —NH(CH$_2$)$_n$OH;

n is 2, 3 or 4

R is vinyl, isopropenyl, t-butylethinyl, hydroxyalkylethinyl, phenylethinyl, cycloalkenyl or phenyl, which may be substituted by halogen, trifluoromethyl, lower alkoxy or nitro;

and X may be —SnBu$_3$, —B(OH)$_2$ or hydrogen.

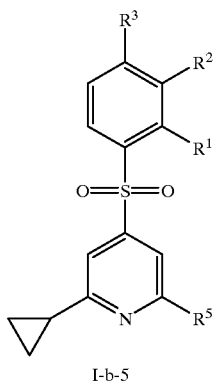

I-b-5 wherein

R¹ is hydrogen;

R² is hydrogen, trifluoromethyl or lower alkyl;

R³ is hydrogen or amino; or

R¹ and R² or R³ and R² taken together are —CH═CH—CH═CH—;

R⁵ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3C_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH₂)$_n$NR⁶R⁷, —N(CH₃)(CH₂)$_n$NR⁶R⁷, —NH(CH₂)$_n$-morpholin-4-yl or —NH(CH₂)$_n$OH;

n is 2, 3 or 4

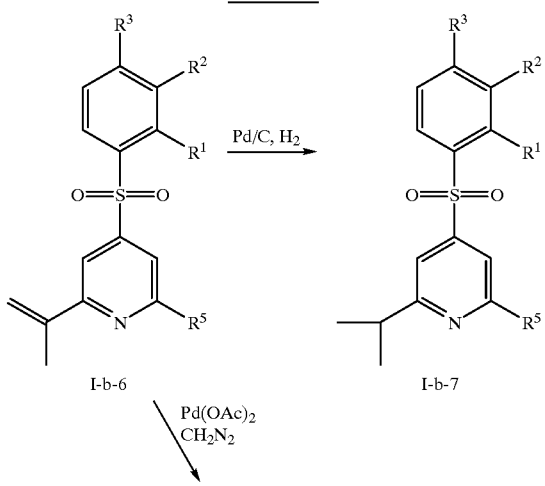

Scheme 10

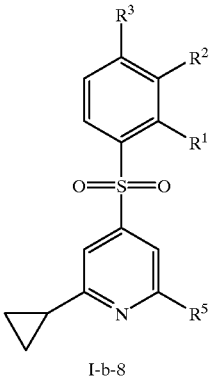

I-b-8 wherein

R¹ is hydrogen;

R² is hydrogen, trifluoromethyl or lower alkyl;

R³ is hydrogen or amino; or

R¹ and R² or R³ and R² taken together are —CH═CH—CH═CH—;

R⁵ is hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-butylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH₂)$_n$NR⁶R⁷, —N(CH₃)(CH₂)$_n$NR⁶R⁷, —NH(CH₂)$_n$-morpholin-4-yl or —NH(CH₂)$_n$OH;

n is 2, 3 or 4

All starting materials are well known compounds or can be prepared by methods known in the art.

As mentioned earlier, the compounds of the present invention possess a selective affinity to 5HT-6 receptors.

The binding of the compounds of formula I in accordance with the invention to 5-HT₆ receptors was determined as follows:

Membranes obtained from HEK 293 cells which had been transfected with 5-HT₆ receptors from rats were used.

The cells were purified by two-fold centrifugation (10 minutes at 3000 g) in phosphate-buffered sodium chloride solution. The cell mass was suspended in an ice-cold solution consisting of 50 mM Tris-HCl buffer, 10 mM MgCl₂, 0.5 mM EDTA and 0.1 mM phenylmethylsulphonyl fluoride and homogenized (Polytron homogenizer, 15 seconds at maximum velocity). The homogenizate was incubated at 37° C. for 10 minutes and subsequently centrifuged (20 minutes at 20 000 g). The cell mass was again suspended in the aforementioned Tris buffer solution. The resulting cell concentration was 4×10⁷ cells/ml. Aliquots each comprising 1 ml of the homogenizate were freeze-dried at (−80)° C.

Displacement tests were carried out in order to determine the affinity of the test substance to the 5-HT₆ receptor. In order to carry out the test, the homogenizate was thawed and suspended in a buffer solution (pH 7.4) consisting of 50 mM Tris-HCl buffer, 5 mM MgCl₂, 10⁻⁵M pargyline and 0.1% ascorbic acid. 100 μl of membrane suspension, 50 μl of [³H]-LSD (specific activity 85 Ci/Mmol, final concentration 1 nM) and 50 μl of test substance solution were incubated at 37° C. for 1 hour. The respective substance was investigated at 7 different concentrations from $10^{-10}$M to $10^{-4}$M. The binding reaction of the test substance was interrupted by rapid filtration through [a] Whatman GF/B filter. The filter was washed with 2×2 ml of Tris-HCl buffer (50 mM, pH 7.4) and the radioactivity on the filter was measured by scintillation spectroscopy in 2 ml of scintillation solution. All tests were carried out in triplicate and were repeated three times.

The pKi values (pKi=$-\log_{10}$Ki) of the test substances have been determined. The Ki value is defined by the following formula:

$$Ki = \frac{IC_{50}}{1 + \frac{(L)}{K_D}}$$

with the $IC_{50}$ values being those concentrations of test compounds in nM by which 50% of the ligands bonded to the receptor are displaced. (L) is the concentration of ligand and the KD value is the dissociation constant of the ligand.

The compounds in accordance with the invention have a selective affinity to 5-HT 6 receptors with a Ki value below 1.6 μM.

The compounds of formula I and the pharmaceutically acceptable salts of he compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises by bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of general formula I as well as their pharmaceutically acceptable salts can be used in the treatment or prevention of central nervous disorders such as depressions, psychoses, schizophrenia, neurological disorders, memory disorders, Parkinson's disease, amoytrophic lateral sclerosis, Alzheimer's disease and Huntington's disease and for the production of corresponding medicaments. The dosage can vary within wide limits and will, of course, be fitted to the individual requirements in each particular case. In the case of oral administration the dosage lies in range of about 0.01 mg per dose to about 1000 mg per day, preferably to about 500 mg of a compound of general formula I or the corresponding amount of a pharmaceutically acceptable salt thereof, although the upper limit can also be exceeded when this is found to be indicated.

The following Examples illustrate the present invention in more detail. However, they are not intended to limit its scope in any manner.

EXAMPLE 1

(4-Benzenesulphonyl-6-bromopyrimidin-2-yl)-methylamine 0.33 g (0.00124 mol) of (4,6-dibromopyrimidin-2-yl)-methylamine and 0.33 g (0.00248 mol) of thiophenol sodium salt were stirred in 15 ml of 1-methyl-2-pyrrolidone at 120° C. for 4 hrs. The solvent was removed and the residue was partitioned between water and diethyl ether. The ether phase was washed with sat. sodium chloride solution and dried over MgSO$_4$. After filtration and removal of the solvent the residue was chromatographed on silica gel with diethyl ether/hexane 1:3 and subsequently dried in a high vacuum. There was obtained 0.24 g (65%) of (4-bromo-6-phenylsulphanylpyrimidin-2-yl)-methylamine as white crystals; m.p.: 122–124° C.

0.10 g (0.0003 mol) of (4-bromo-6-phenylsulphanylpyrimidin-2-yl)-methylamine was dissolved in 20 ml of MeOH and treated with a solution of 1.80 g (0.0085 mmol) of NaIO$_4$. The suspension was stirred at 60° C. for 24 hrs. Subsequently, the solvent was removed and the residue was partitioned in water and diethyl ether. The ether phase was washed with sat. sodium chloride solution and dried over MgSO$_4$. After filtration and removal of the solvent the residue was chromatographed on silica gel with ethyl acetate/hexane 1:4 and subsequently dried in a high vacuum. There was obtained 0.054 g (55%) of (4-benzenesulphonyl-6-bromopyrimidin-2-yl)-methylamine as white crystals; m.p.: 142–143° C.

EXAMPLE 2

[4-(4-Amino-benzenesulphonyl)-6-bromopyrimidin-2-yl]-methylamine 0.70 g (0.0026 mol) of (4,6-dibromopyrimidin-2-yl)-methylamine and 0.56 g (0.0026 mol) of 4-nitrothiophenol potassium salt were dissolved in 15 ml of 1-methyl-2-pyrrolidone and stirred at 50° C. for 5 hrs. The solvent was removed and the residue was partitioned in water and ethyl acetate. The combined organic phases were washed with sat. sodium chloride solution and dried over MgSO$_4$. After filtration and removal of the solvent the residue was chromatographed on silica gel with ethyl acetate/hexane 1:9 and subsequently dried in a high vacuum. There was obtained 0.50 g (56%) of [4-bromo-6-(4-nitrophenylsulphanyl)-pyrimidin-2-yl]-methylamine as yellow crystals; m.p.: 204–205° C.

0.17 g (0.0005 mol) of [4-bromo-6-(4-nitrophenylsulphanyl)-pyrimidin-2-yl]-methylamine was dissolved in 30 ml of dichloromethane and treated with 0.35 g (0.0011 mol) of meta-chloroperbenzoic acid. After stirring at room temperature for 3 hrs. the reaction mixture was extracted with sat. Na$_2$CO$_3$ solution, water and sat. sodium chloride solution and dried over MgSO$_4$. After filtration and removal of the solvent the residue was chromatographed on silica gel with ethyl acetate/hexane 1:4 and subsequently dried in a high vacuum. There was obtained 0.10 g (53%) of [4-bromo-6-(4-nitrobenzenesulphonyl)-pyrimidin-2-yl]-methylamine as beige crystals; m.p.: 185–186° C.

0.40 g (0.0011 mol) of [4-bromo-6-(4-nitrobenzenesulphonyl)-pyrimidin-2-yl]-methylamine was suspended in 20 ml of acetic acid, treated with 0.40 g of iron powder and heated to 60° C. for about 4 hrs. Thereafter, the solvent was removed, the residue was digested in water and the precipitate which thereby separated was isolated. This was dissolved in dichloromethane and dried over MgSO$_4$. After filtration and removal of the solvent the residue was chromatographed on silica gel with ethyl acetate/hexane 1:2 and subsequently dried in a high vacuum. There was obtained 0.25 g (68%) of [4-(4-amino-benzenesulphonyl)-6-bromopyrimidin-2-yl]-methylamine as a yellow solid; m.p.: >250° C.

EXAMPLE 3

(4-Benzenesulphonyl-6-bromopyridin-2-yl)-methylamine 0.50 g (0.00177 mol) of 4-nitro-2,6-dibromopyridine and 0.29 g (0.00177 mol) of benzenesulphinic acid sodium salt were dissolved in 17 ml of dimethylformamide and stirred at 50° C. for 1 hr. The solvent was removed and the residue was partitioned in water and ethyl acetate. The combined organic phases were washed with sat. sodium chloride solution and dried over MgSO$_4$. After filtration and removal of the solvent the residue was chromatographed on silica gel with ethyl acetate/hexane 1:4 and subsequently dried in a high vacuum. There was obtained 0.59 g (88.5%) of 4-benzenesulphonyl-2,6-dibromopyridine as white crystals; m.p.: 134–135° C.

0.42 g (0.00112 mol) of 4-benzenesulphonyl-2,6-dibromopyridine and 1.4 ml of 8M methylamine in ethanol were stirred at room temperature in a mixture of 11 ml of ethanol and 11 ml of dioxane for 48 hrs. After removal of the solvent the residue was chromatographed on silica gel with ethyl acetate/hexane 1:10. The product-containing fractions were suspended in 25 ml of diethyl ether, treated in an ultrasound bath and diluted with 45 ml of hexane. The suspension was suction filtered and the filter material was dried in a high vacuum. There was obtained 0.224 g (61%) of (4-benzenesulphonyl-6-bromopyridin-2-yl)-methylamine as white crystals; m.p.: 145–148° C.

EXAMPLE 4

(4-Benzenesulphonylpyridin-2-yl)-methylamine 0.09 g (0.000275 mol) of (4-benzenesulphonyl-6-bromopyridin-2-yl)-methylamine was dissolved in 7 ml of ethanol, treated with 0.009 g of Pd/C (10%) and hydrogenated under normal pressure for 18 hrs. Thereafter, the catalyst was filtered off, the solvent was removed and the residue was partitioned in ethyl acetate and saturated bicarbonate solution. The organic phase was washed with sat. sodium chloride solution and dried over MgSO$_4$. After removal of the solvent the residue was chromatographed on silica gel with ethyl acetate/hexane 1:4 and 1:3. There was obtained 0.025 g (37%) of (4-benzenesulphonylpyridin-2-yl)-methylamine as beige crystals; m.p.: 142–143° C.

EXAMPLE 5

(4-Benzenesulphonyl-6-bromopyridin-2-yl)-dimethylamine 0.113 g (0.0003 mol) of 4-benzenesulphonyl-2,6-dibromopyridine and 0.54 ml of 5.6 M dimethylamine in ethanol were stirred at room temperature in a mixture of 3 ml of ethanol and 3 ml of dioxan for 5 hrs. After removal of the solvent the residue was chromatographed on silica gel with ethyl acetate/hexane 1:10. There was obtained 0.09 g (88%) of (4-benzenesulphonyl-6-bromopyridin-2-yl)-dimethylamine as white crystals; m.p. 128–130° C.

EXAMPLE 6

4-(2,6-dibromopyridine-4-sulphonyl)-phenylamine 0.48 g (0.0025 mol) of 2,6-dibromo-4-nitropyridine and 0.70 g (0.0024 mol) of 4-nitrothiophenol potassium salt were dissolved in 12.5 ml of dimethylformamide and stirred at room temperature for 3 hrs. The solvent was removed and the residue was partitioned in water and ethyl acetate. The combined organic phases were washed with sat. sodium chloride solution and dried over MgSO$_4$. After filtration and removal of the solvent the residue was chromatographed on silica gel with ethyl acetate/hexane 1:19 and subsequently dried in a high vacuum. There was obtained 0.785 g (81%) of 2,6-dibromo-4-(4-nitrophenylsulphanyl)-pyridine as yellow crystals; m.p. 166–168° C.

23.6 g (0.0605 mol) of 2,6-dibromo-4-(4-nitrophenylsulphanyl)-pyridine were dissolved in 0.5 l of dichloromethane and treated with 33.0 g (0.134 mol) of meta-chloroperbenzoic acid (70%). The mixture was stirred at room temperature for 2 hrs. Subsequently, the reaction mixture was extracted with sat. Na$_2$CO$_3$ solution and sat. sodium chloride solution, dried over MgSO$_4$ and, after filtration and removal of the solvent, chromatographed on silica gel with dichloromethane/hexane 1:1 and 2:1. There were obtained 22.30 g (87%) of 2,6-dibromo-4-(4-nitrobenzenesulphonyl)-pyridine as yellowish crystals; m.p.: 204–206° C.

22.30 g (0.052 mol) of 2,6-dibromo-4-(4-nitrobenzenesulphonyl)-pyridine were suspended in a mixture of 275 ml of methanol and 275 ml of dioxane, treated with 22.30 g of powdered iron and a solution of 22.30 g of NH$_4$Cl in 550 ml of water and heated at reflux for 1.5 hrs. Then, the organic solvents were distilled off on a rotary evaporator and the residue was diluted with 1.0 l of dichloromethane and suction filtered. The filter material was suspended in a mixture of 250 ml of methanol and 250 ml of dichloromethane in an ultrasound bath, again suction filtered and the filtrate was retained. The first filtrate was separated in a separating funnel and the organic phase was washed with sat. sodium chloride solution, dried over MgSO$_4$, filtered and concentrated together with the second filtrate. The residue was chromatographed on silica gel with dichloromethane. There were obtained 16.6 g (80%) of 4-(2,6-dibromopyridine-4-sulphonyl)-phenylamine as yellowish crystals; m.p.: 196–198° C. (dec.).

EXAMPLE 7

4-(2,6-Diiodo-pyridine-4-sulfonyl)-phenylamine 0.52 g (0.00133 Mol) 4-(2,6-Dibromo-pyridine-4-sulfonyl)-phenylamine and 0.45 g (0.003 Mol) NaI were stirred in aqueous HI (10 ml) at 120° C. for 5 h. Then the reaction mixture was diluted with water, extracted with ethyl acetate, the organic phase was washed with sat. bicarbonate and brine, dried over MgSO$_4$ and evaporated. After chromatography on SiO2 with ethyl acetate hexane 1:3 and drying in a high vacuum it was obtained 0.255 g (42%) 4-(2,6-diiodo-pyridin-4-ylsulfanyl)-phenylamine as a brown solid; mp.: 175–176° C.

0.227 g (0.0005 Mol) 4-(2,6-Diiodo-pyridin-4-ylsulfanyl)-phenylamine were dissolved in CH$_2$Cl$_2$ (10 ml) and treated with 0.27 g (0.0011 Mol) of mCPBA (70%) for 3 h at ambiente temperature. Then the solvent was removed, the residue dissolved in ethyl acetate, washed with sat. bicarbonate and brine, dried over MgSO$_4$ and evaporated. After chromatography on SiO2 with ethyl acetate hexane 1:2 and drying in a high vacuum it was obtained 0.156 g (68%) of 4-(2,6-diiodo-pyridine-4-sulfonyl)-phenylamine as a brownish solid. MS (EI): me/e 486 (M$^+$).

EXAMPLE 8

4-(4-Aminobenzenesulphonyl)-6-bromopyridin-2-ylamine 0.48 g (0.0025 mol) of 2,6-dibromo-4-nitropyridine and 0.70 g (0.0024 mol) of 4nitrothiophenol potassium salt were dissolved in 12.5 ml of dimethylformamide and stirred at room temperature for 3 hrs. The solvent was removed and the residue was partitioned in water and ethyl acetate. The combined organic phases were washed with sat. sodium chloride solution and dried over MgSO$_4$. After filtration and removal of the solvent the residue was chromatographed on silica gel with ethyl acetate/hexane 1:19 and subsequently dried in a high vacuum. There was obtained 0.785 g (81%) of 2,6-dibromo-4-(4-nitrophenylsulphanyl)-pyridine as yellow crystals; m.p. 166–168° C.

23.6 g (0.0605 mol) of 2,6-dibromo-4-(4-nitrophenylsulphanyl)-pyridine were dissolved in 0.5 l of dichloromethane and treated with 33.0 g (0.134 mol) of meta-chloroperbenzoic acid (70%). The mixture was stirred at room temperature for 2 hrs. Subsequently, the reaction mixture was extracted with sat. Na$_2$CO$_3$ solution and sat. sodium chloride solution, dried over MgSO$_4$ and, after filtration and removal of the solvent, chromatographed on silica gel with dichloromethane/hexane 1:1 and 2:1. There were obtained 22.30 g (87%) of 2,6-dibromo-4-(4-nitrobenzenesulphonyl)-pyridine as yellowish crystals; m.p.: 204–206° C.

22.30 g (0.052 mol) of 2,6-dibromo-4-(4-nitrobenzenesulphonyl)-pyridine were suspended in a mixture of 275 ml of methanol and 275 ml of dioxane, treated with 22.30 g of powdered iron and a solution of 22.30 g of NH$_4$Cl in 550 ml of water and heated at reflux for 1.5 hrs. Then, the organic solvents were distilled off on a rotary evaporator and the residue was diluted with 1.0 l of dichloromethane and suction filtered. The filter material was suspended in a mixture of 250 ml of methanol and 250 ml of dichloromethane in an ultrasound bath, again suction filtered and the filtrate was retained. The first filtrate was separated in a separating funnel and the organic phase was washed with sat. sodium chloride solution, dried over MgSO$_4$, filtered and concentrated together with the second filtrate. The residue was chromatographed on silica gel with dichloromethane. There were obtained 16.6 g (80%) of 4-(2,6-dibromopyridine-4-sulphonyl)-phenylamine as yellowish crystals; m.p.: 196–198° C. (dec.).

0.196 g (0.0005 mol) of 4-(2,6-dibromopyridine-4-sulphonyl)-phenylamine was dissolved in 10 ml of dioxane, treated with 1.0 ml of sat. NH$_3$ in methanol and stirred in an autoclave at 130° C. for 72 hrs. After removal of the solvent the residue was taken up in ethyl acetate, washed with sat. NH$_4$Cl solution, water and sat. sodium chloride solution, dried over MgSO$_4$ and the solvent was removed. The residue was chromatographed on silica gel with ethyl acetate/hexane 1:2 and 1:1. There was obtained 0.117 g (71%) of 4-(4-aminobenzenesulphonyl)-6-bromopyridin-2-ylamine as a yellowish, amorphous solid; m.p.: 204–205° C.

EXAMPLE 9

[4-(4-Aminobenzenesulphonyl)-6-bromopyridin-2-yl]-methylamine 1.45 g (0.0037 mol) of 4-(2,6-dibromopyridine-4-sulphonyl)-phenylamine were dissolved in 40 ml of dioxane and treated with 9.6 ml of 8M methylamine in ethanol. The mixture was stirred at room temperature for 48 hrs., the solvents were removed and the residue was chromatographed on silica gel with ethyl acetate/hexane 1:3 and 1:2. The product-containing fractions, after concentration, were suspended in 50 ml of diethyl ether, treated in an ultrasound bath for 1 hr., then treated with 75 ml of hexane and the precipitate which thereby resulted was filtered off under suction. After drying in a high vacuum there was obtained 0.87 g (69%) of [4-(4-aminobenzenesulphonyl)-6-bromopyridin-2-yl]-methylamine as pale beige crystals; m.p.: 171–173° C.

EXAMPLE 10

[4-(4-Aminobenzenesulphonyl)-6-bromopyridin-2-yl]-dimethylamine 0.07 g (0.000179 mol) of 4-(2,6-dibromopyridine-4-sulphonyl)-phenylamine was dissolved in 1.5 ml of dioxane and treated with 3.0 ml of 5.6M dimethylamine in ethanol. The mixture was stirred at room temperature for 2 hrs., the solvents were removed and the residue was chromatographed on silica gel with ethyl acetate/hexane 1:1 and 1:3. There was obtained 0.04 g (63%) of [4-(4-aminobenzenesulphonyl)-6-bromopyridin-2-yl]-dimethylamine as yellowish crystals; m.p.: 170–172° C. (dec.).

EXAMPLE 11

4-(2-Chloro-6-pyrrolidin-1-yl-pyridine-4-sulfonyl)-phenylamine)

To a solution of 63.7 g (0.226 Mol) 2,6-dibromo-4-nitropyridine in dimethylformamide (600 ml) at −15° C. were slowly added 50.0 g (0.226 Mol) 4-acetamidobenzenesulfinic acid sodium salt. The mixture was stirred at 15° C. for 3.5 h. Then 2.0 l water were added. It was stirred for another hour, filtered and the residue on the filter was washed with water (150 ml). It was then dissolved in aceton (hot, 700 ml) and evaporated. The residue was suspended in toluene (700 ml) and evaporated, again suspended in toluene and filtered. The residue on the filter was washed with toluene (200 ml) and dried in a high vacuum. It was obtained 67.3 g (69%) N-[4-(2,6-dibromo-pyridine-4-sulfonyl)-phenyl]-acetamide as a bright beige powder; mp.: 211° C.

30.0 g (0.069 Mol) N-[4-(2,6-dibromo-pyridine-4-sulfonyl)-phenyl]-acetamide were dissolved in a mixture of dioxane (120 ml) and conc. HCl (166 ml) and stirred at 78° C. for 6 h. After cooling to ambiente temperature water (750 ml) was added and the suspension was filtered. The residue on the filter was washed with water and dried in a high vacuum. It was obtained 16.9 g (81%) 4-(2,6-dichloro-pyridine-4-sulfonyl)-phenylamine as a bright yellow powder; mp.: 190–192° C.

16.8 g (0.0554 Mol) 4-(2,6-dichloro-pyridine-4-sulfonyl)-phenylamine were dissolved in dioxane (165 ml), 23.0 ml (0.2753 Mol) pyrrolidine were added at ambiente temperature and stirred for 1.5 h. The reaction mixture was then poured onto water (600 ml), stirred for 1 h and filtered. The residue on the filter was washed with water (150 ml), dissolved in tetrahydrofuran (250 ml) and treated with $Na_2SO_4$ (20.0 g) and Norit-SX-1 (1.7 g). After filtration the residue on the filter was washed with tetrahydrofuran (100 ml) and subsequently dried in a high vacuum. It was obtained 18.4 g (98%) 4-(2-chloro-6-pyrrolidin-1-yl-pyridine-4-sulfonyl)-phenylamine as a bright yellow powder; mp.: 225–226° C.

EXAMPLE 12

4-(2-Bromo-6-pyrrolidin-1-yl-pyridine-4-sulphonyl)-phenylamine 1.0 g (0.00255 mol) of 4-(2,6-dibromopyridine-4-sulphonyl)-phenylamine was dissolved in 25 ml of dioxane and treated with 2.1 ml of pyrrolidine. The mixture was stirred at room temperature for 4 hrs., the solvent was removed and the residue was chromatographed on silica gel with ethyl acetate/hexane 1:1. There was obtained 0.9 g (93%) of 4-(2-bromo-6-pyrrolidin-1-yl-pyridine-4-sulphonyl)-phenylamine as beige crystals; m.p.: 216° C. (dec).

EXAMPLE 13

4-(2-Iodo-6-pyrrolidin-1-yl-pyridine-4-sulfonyl)-phenylamine 0.127 g (0.000261 Mol) 4-(2,6-Diiodo-pyridine-4-sulfonyl)-phenylamine were dissolved in dioxane (5 ml) and treated with 0.22 ml (0.0026 Mol) pyrrolidine for 6 h at ambiente temperature. Then the solvent was removed, the residue dissolved in ethyl acetate, washed with 1N HCl, sat. bicarbonate and brine, dried over $MgSO_4$ and evaporated. After chromatography on SiO2 with ethyl acetate hexane 1:2 and drying in a high vacuum it was obtained 0.084 g (75%) of 4-(2-iodo-6-pyrrolidin-1-yl-pyridine-4-sulfonyl)-phenylamine as a beige solid; mp.: 218–221° C. (dec.).

EXAMPLE 14

4-(2-Pyrrolidin-1-yl-pyridine-4-sulfonyl)-phenylamine 10.0 g (0.026 Mol) 4-(2-Bromo-6-pyrrolidin-1-yl-pyridine-4-sulfonyl)-phenylamine were dissolved in tetrahydrofuran (200 ml), cooled at −40° C. and 33 ml (0.053 Mol) nBuLi in hexane were added. The reaction mixture was stirred at −15° C. for 1 h. Then water (10 ml) was added, the mixture was extracted with ethylacetate, the organic phase was washed with water and brine and dried over $Na_2SO_4$. After chromatography on $SiO_2$ with ethyl acetate hexan 1:1 and drying in a high vacuum, it was obtained 3.6 g (45%) of 4-(2-pyrrolidin-1-yl-pyridine-4-sulfonyl)-phenylamine as light yellow cristals; mp.: 186–187° C.

EXAMPLE 15

4-(2-Pyrrolidin-1-yl-6-vinyl-pyridine-4-sulfonyl)-phenylamine)

0.38 g (0.001 Mol) 4-(2-Bromo-6-pyrrolidin-1-yl-pyridine-4-sulfonyl)-phenylamine, 0.116 g (0.0001 Mol) $Pd(PPh_3)_4$ and 0.292 ml (0.001 Mol) vinyl-tributylstannane were stirred at reflux for 18 h in a mixture of dioxane (10 ml) and 2N $Na_2CO_3$ (2 ml). Then the solvent was evaporated, the residue was taken up in ethyl acetate, washed with water and brine and dried over $Na_2SO_4$. After chromatography on $SiO_2$ with ethyl acetate hexane 2:3 the product containing fractions were evaporated and the residue taken up in hexane. The suspension was stirred for 1 h and then filtered. The residue on the filter was washed with hexane (10 ml) and dried in a high vacuum. It was obtained 0.16 g (49%) 4-(2-pyrrolidin-1-yl-6-vinyl -pyridine-4-sulfonyl)-phenylamine as a yellow solid; mp.: 181–182° C.

EXAMPLE 16

4-(2-Ethyl-6-pyrrolidin-1-yl-pyridine-4-sulfonyl)-phenylamine 0.12 g (0.00036 Mol) 4-(2-Pyrrolidin-1-yl-6-vinyl-pyridine-4-sulfonyl)-phenylamine were dissolved in ethanol (36 ml) and hydrogenated under an atmosphere of $H_2$-gas with a catalytic amount of Pd/C (10%) at ambiente temperature for 3 h. After filtration and evaporation of the solvent the residue was chromatographed on $SiO_2$ with ethyl acetate hexane 1:2. After drying in a high vacuum it was obtained 0.10 g (83%) 4-(2-ethyl-6-pyrrolidin-1-yl-pyridine-4-sulfonyl)-phenylamine as an offwhite solid; mp.: 154–155° C.

EXAMPLE 17

4-(2-Isopropyl-6-pyrrolidin-1-yl-pyridine-4-sulfonyl)-phenylamine 0.56 g (0.0015 Mol) 4-(2-Bromo-6-pyrrolidin-1-yl-pyridine-4-sulfonyl) -phenylamine, 0.171 g (0.00015 Mol) $Pd(PPh_3)_4$ and 0.191 g (0.0021 Mol) isopropenyl boronic acid were stirred at reflux for 18 h in a mixture of dioxane (10 ml) and 2N $Na_2CO_3$ (4 ml). Then the solvent was evaporated, the residue was taken up in ethyl acetate, washed with water and brine and dried over $Na_2SO_4$. After chromatography on $SiO_2$ with ethyl acetate hexane 1:2 the product containing fractions were evaporated and the residue taken up in hexane. The suspension was stirred for 1 h and then filtered. The residue on the filter was washed with hexane (10 ml) and dried in a high vacuum. It was obtained 0.265 g (52%) 4-(2-isopropenyl-6-pyrrolidin-1-yl-pyridine-4-sulfonyl)-phenylamine as a light yellow solid; mp.: 200–201° C.

0.05 g (0.0001456 Mol) 4-(2-Isopropenyl-6-pyrrolidin-1-yl-pyridine-4-sulfonyl)-phenylamine were dissolved in ethanol (5 ml) and hydrogenated under an atmosphere of $H_2$-gas with a catalytic amount of Pd/C (10%) at ambiente temperature for 3 h. After filtration and evaporation of the solvent the residue was chromatographed on $SiO_2$ with ethyl acetate hexane 1:2. After drying in a high vacuum it was obtained 0.046 g (92%) 4-(2-isopropyl-6-pyrrolidin-1-yl-pyridine-4-sulfonyl)-phenylamine as a white solid; mp.: 148–150° C.

EXAMPLE 18

4-($^2$-Cyclopropyl-6-pyrrolidin-1-yl-pyridine-4-sulfonyl)-phenylamine 0.165 g (0.0005 Mol) 4-(2-Pyrrolidin-1-yl-6-vinyl-pyridine-4-sulfonyl)-phenylamine were dissolved in ethyl ether (100 ml) and cooled to 0° C. A solution of diazomethane in ethyl ether (30 ml) was carefully added. Upon addition of a catalytic amount of Pd(OAc)$_2$ gas evolution started. The reaction mixture was allowed to warm to ambient temperature and stirred for 30 min. After addition of a few drops of acetic acid the solvent was evaporated and the residue chromatographed on SiO$_2$ with ethyl acetate hexane 1:2. It was obtained 0.149 g (87%) of 4-(2-cyclopropyl-6-pyrrolidin-1-yl-pyridine-4-sulfonyl)-phenylamine as bright yellow cristals; mp.: 216–218° C.

EXAMPLE 19

4-(2-cyclohex-1-enyl-6-pyrrolidine-1-yl-pyridine-4-sulfonyl)-phenylamine

A mixture of 382 mg (1 mmole) 4-(2-bromo-6-pyrrolidine-1-yl-pyridine-4-sulfonyl)-phenylamine, 371 mg (1 mmole) tributyl-cyclohex-1-enyl stannane, and 70 mg bis(triphenylphosphine)-palladium(II)-chloride in 20 ml dimethylformamide is stirred for 3 hours at 80° C. The solvent is removed and the residue is diluted with dichloromethane. The dichloromethane solution is washed twice with saturated aqueous potassium fluoride, dried over magnesiumsulfate and concentrated in vacuo. Flash chromatography of the residue (silicagel, hexane/AcOEt 3/1) yields 191 mg (50%) pure 4-(2-cyclohex-1-enyl-6-pyrrolidine-1-yl-pyridine-4-sulfonyl)-phenylamine as a white solid. mp 237–238° C.

EXAMPLE 20

4-(2-Phenyl-6-pyrrolidine-1-yl-pyridine-4-sulfonyl)-phenylamine

A mixture of 191 mg (0.5 mmole) 4-(2-bromo-6-pyrrolidine-1-yl-pyridine-4-sulfonyl)-phenylamine, 60.9 mg (0.5 mmole) benzene-boronic acid, 55 mg sodium carbonate and 18 mg bis(triphenylphosphine)-palladium(II)-chloride is refluxed for 18 hours in 5 ml 1,2-dimethoxyethane and 0.25 ml water. The solvent is removed and the residue is diluted with dichloromethane. The dichloromethane solution is washed twice with water, dried over magnesiumsulfate and concentrated in vacuo. Flash chromatography (silicagel, ethyl acetate/hexane 1/1) of the residue yields 130 mg (68%) pure 4-(2-phenyl-6-pyrrolidine-1-yl-pyridine-4-sulfonyl)-phenylamine as a pale yellow soild mp.: 255–258° C.

EXAMPLE 21

4-[2-(3,3-Dimethyl-but-1-ynyl)-6-pyrrolidine-1-yl-pyridine-4-sulfonyl]-phenylamine A mixture of 382 mg (1 mmole) 4-(2-bromo-6-pyrrolidine-1-yl-pyridine-4-sulfonyl)-phenylamine, 91 mg (1.1 mmole) 3,3-dimethyl-1-butyne, 38 mg copper(I)-iodide and 35 mg bis(triphenylphosphine)-palladium(II)-chloride is refluxed for 1 hour in 5 ml dimethylformamide and 5 ml diethylamine. The solvents are removed and the residue is diluted with dichloromethane. The dichloromethane solution is washed twice with water, dried over magnesiumsulfate and concentrated in vacuo. Recrystallisation of the residue from ethanol yields 250 mg (65%) pure 4-[2-(3,3-dimethyl-but-1-ynyl)-6-pyrrolidine-1-yl-pyridine-4-sulfonyl]-phenylamine als a light brown solid mp.: 242–244° C.

EXAMPLE 22

4-[4-(4-Amino-benzenesulfonyl)-6-pyrrolidine-1-yl-pyridine-2-yl]-2-methyl-but-3-yn-2-ol A mixture of 382 mg (1 mmole) 4-(2-bromo-6-pyrrolidine-1-yl-pyridine-4-sulfonyl)-phenylamine, 93 mg (1.1 mmole) 2-methyl-3-butyn-2-ol, 38 mg copper(I)-iodide and 35 mg bis(triphenylphosphine)-palladium(II)-chloride is refluxed for 1 hour in 5 ml dimethylformamide and 5 ml diethylamine. The solvents are removed and the residue is diluted with dichloromethane. The dichloromethane solution is washed twice with water, dried over magnesiumsulfate and concentrated in vacuo. Flash chromatography (silicagel, hexane/ethyl acetate 7/3 ) and recrystallisation of the residue from ethanol yields 200 mg (52%) pure 4-[4-(4-amino-benzenesulfonyl)-6-pyrrolidine-1-yl-pyridine-2-yl]-2-methyl-but-3-yn-2-ol als a white solid mp.: 168–170° C.

EXAMPLE 23

4-(2-Phenylethynyl-6-pyrrolidine-1-yl-pyridine-4-sulfonyl)-phenylamine

A mixture of 382 mg (1 mmole) 4-(2-bromo-6-pyrrolidine-1-yl-pyridine-4-sulfonyl)-phenylamine, 112 mg (1.1 mmole) phenylacetylene, 38 mg copper(I)-iodide and 35 mg bis(triphenylphosphine)-palladium(II)-chloride in 5 ml dimethylformamide and 5 ml diethylamine is refluxed for 2 hours. The solvents are removed and the residue is diluted with dichloromethane. The dichloromethane solution is washed twice with water, dried over magnesiumsulfate and concentrated in vacuo. Recrystallisation of the residue from chloroform/ethanol yields 260 mg (64%) pure 4-(2-phenylethynyl-6-pyrrolidine-1-yl-pyridine-4-sulfonyl)-phenylamine als a pale yellow solid mp.: 202–204° C.

EXAMPLE 24

4-[2-(2-Methoxy-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 84 mg (0.55 mmole) 2-methoxyphenylboronic acid, 25 mg sodium carbonate and
18 mg bis(triphenylphosphine)-palladium(II)-chloride is refluxed for 18 hours in 5 ml 1,2-dimethoxyethane and 0.25 ml water. The solvent is removed and the residue is diluted with dichloromethane. The dichloromethane solution is washed twice with water, dried over magnesiumsulfate and concentrated in vacuo. Flash chromatography (silicagel, ethyl acetate/hexane 1/1 ) of the residue yields 100 mg (48%) pure 4-[2-(2-methoxy-phenyl)-6-pyrrolidine-1-yl-pyridine-4-sulfonyl]-phenylamine as a pale yellow solid mp.: 217–219° C.

EXAMPLE 25

4-[2-(3,5-bis-Trifluoromethyl-phenyl)-6-pyrrolidin-1-yl-pyridine-4-sulfonyl]-phenylamine A mixture of 191 mg (0.5 mmole) 4-(2-bromo-6-pyrrolidine-1-yl-pyridine-4-sulfonyl)-phenylamine, 142 mg (0.55 mmole) 3,5-bis(trifluormethyl)phenylboronic acid, 25 mg sodium carbonate and 20 mg bis(triphenylphosphine)-palladium(II)-chloride is refluxed for 48 hours in 10 ml 1,2-dimethoxyethane and 1 ml water. The solvent is removed and the residue is diluted with dichloromethane. The dichloromethane solution is washed twice with water, dried over magnesiumsulfate and concentrated in vacuo. Flash chromatography (silicagel, ethyl acetate/hexane 1/1 ) of the residue yields 84 mg (32%) pure 4-[2-(3,5-bis-trifluoromethyl-phenyl)-6-pyrrolidine-1-yl-pyridine-4-sulfonyl]-phenylamine as a pale yellow solid mp.: 184–186° C.

EXAMPLE 26

4-[2-(2-Chloro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 86 mg (0.55 mmole) 2-chlorophenylboronic acid, 25 mg sodium carbonate and
18 mg bis(triphenylphosphine)-palladium(II)-chloride is refluxed for 18 hours in 5 ml 1,2-dimethoxyethane and 0.25 ml water. The solvent is removed and the residue is diluted with dichloromethane. The dichloromethane solution is washed twice with water, dried over magnesiumsulfate and concentrated in vacuo. Flash chromatography (silicagel, ethyl acetate/hexane 1/1 ) of the residue yields 100 mg (48%) pure 4-[2-(2-chloro-phenyl)-6-pyrrolidine-1-yl-pyridine-4-sulfonyl]-phenylamine as a pale yellow solid mp.: 188–190° C.

EXAMPLE 27

4-[2-(4-Chloro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 86 mg (0.55 mmole) 4-chlorphenylboronic acid, 18 mg bis(triphenylphosphine)-palladium(II)-chloride is refluxed for 1.5 hours in 7 ml toluene and 2 ml 2N aqueous potassium carbonate. The solvents are removed in vacuo. Flash chromatography (silicagel, ethyl acetate/hexane 1/1) of the residue yields 147 mg (71%) pure 4-[2-(4-chloro-phenyl)-6-pyrrolidine-1-yl-pyridine-4-sulfonyl]-phenylamine as a white solid mp.: 236–237° C.

EXAMPLE 28

4-[2-(3-Methoxy-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 84 mg (0.55 mmole) 3-methoxyphenylboronic acid, 25 mg sodium carbonate and
18 mg bis(triphenylphosphine)-palladium(II)-chloride is refluxed for 19 hours in 5 ml 1,2-dimethoxyethane and 0.25 ml water. The solvent is removed and the residue is diluted with methylenchloride. The methylenchloride solution is washed twice with water, dried over magnesiumsulfate and concentrated in vacuo. Flash chromatography (silicagel, ethyl acetate/hexane 1/1 ) of the residue yields 73 mg (36%) pure 4-[2-(3-methoxy-phenyl)-6-pyrrolidine-1-yl-pyridine-4sulfonyl]-phenylamine as a pale yellow solid mp.: 214–215° C.

EXAMPLE 29

4-[2-(4-Fluoro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 77 mg (0.55 mmole) 4-fluorophenylboronic acid, 18 mg bis(triphenylphosphine)-palladium(II)-chloride is refluxed for 2 hours in 7 ml toluene and 2 ml 2N aqueous potassium carbonate. The solvents are removed in vacuo. Flash chromatography (silicagel, ethyl acetate/hexane 1/1) of the residue yields 45 mg (22%) pure 4-[2-(4-fluoro-phenyl)-6-pyrrolidine-1-yl-pyridine-4-sulfonyl]-phenylamine as a white solid mp.: 245–246° C.

EXAMPLE 30

4-[2-(4-Methoxy-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 77 mg (0.55 mmole) 4-methoxyphenylboronic acid, 18 mg bis(triphenylphosphine)-palladium(II)-chloride is refluxed for 2 hours in 7 ml toluene and 2 ml 2N aqueous potassium carbonate. The solvents are removed in vacuo. Flash chromatography (Silicagel, ethyl acetate/hexane 1/1) of the residue yields 145 mg (70%) pure 4-[2-(4-methoxy-phenyl)-6-pyrrolidine-1-yl-pyridine-4-sulfonyl]-phenylamine as a pale yellow solid mp.: 227–229° C.

EXAMPLE 31

4-[2-(3-Chloro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 84 mg (0.55 mmole) 3-chlorophenylboronic acid, 18 mg bis(triphenylphosphine)-palladium(II)-chloride is refluxed for 2 hours in 7 ml toluene and 2 ml 2N aqueous potassium carbonate. The solvents are removed in vacuo. Flash chromatography (silicagel, ethyl acetate/hexane 1/1) of the residue yields 47 mg (22%) pure 4-[2-(3-chloro-phenyl)-6-pyrrolidine-1-yl-pyridine-4-sulfonyl]-phenylamine as a pale yellow solid mp.: 260–261° C.

EXAMPLE 32

4-(2-Pyrrolidin-1-yl-6-p-tolyl-pyridine-4-sulfonyl)-phenylamine

A mixture of 191 mg (0.5 mmole) 4-(2-bromo-6-pyrrolidine-1-yl-pyridine-4-sulfonyl)-phenylamine, 84 mg (0.55 mmole) 4-tolylboronic acid, 18 mg bis(triphenylphosphine)-palladium(II)-chloride is refluxed for 2.5 hours in 7 ml toluene and 2 ml 2N aqueous potassium carbonate. The solvents are removed in vacuo. Flash chromatography (silicagel, ethyl acetate/hexane 1/1) of the residue yields 80 mg (40%) pure 4-(2-pyrrolidine-1-yl-6-p-tolyl-pyridine-4-sulfonyl)-phenylamine as a pale yellow solid mp.: 250–251° C.

EXAMPLE 33

4-[2-Pyrrolidin-1-yl-6-(3-trifluoromethyl-phenyl )-pyridine-4-sulfonyl]-phenylamine A mixture of 191 mg (0.5 mmole) 4-(2-bromo-6-pyrrolidine-1-yl-pyridine-4-sulfonyl)-phenylamine, 106 mg (0.55 mmole) 3-(trifluoromethyl)phenylboronic acid,
18 mg bis(triphenylphosphine)-palladium(II)-chloride is refluxed for 2 hours in 7 ml toluene and 2 ml 2N aqueous potassium carbonate. The solvents are removed in vacuo. Flash chromatography (silicagel, ethyl acetate/hexane 1/1) of the residue yields 186 mg (83%) pure 4-[2-pyrrolidine-1-yl-6-(3-trifluoromethyl-phenyl)-pyridine-4-sulfonyl]-phenylamine as a pale yellow solid mp.: 219–220° C.

EXAMPLE 34

4-[2-(3-Nitro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 92 mg (0.55 mmole) 3-nitrophenylboronic acid, 18 mg bis (triphenylphosphine)-palladium(II)-chloride is refluxed for 2.5 hours in 7 ml toluene and 2 ml 2N aqueous potassium carbonate. The solvents are removed in vacuo. Flash chromatography (silicagel, ethyl acetate/hexane 1/1) of the residue yields 102 mg (48%) pure 4-[2-(3-nitro-phenyl)-6-pyrrolidine-1-yl-pyridine-4-sulfonyl]-phenylamine as a yellow solid mp.: 249–251° C.

EXAMPLE 35

4-(2-Pyrrolidin-1-yl-6-thiophen-3-yl-pyridine-4-sulfonyl)-]-phenylamine

A mixture of 191 mg (0.5 mmole) 4-(2-bromo-6-pyrrolidine-1-yl-pyridine-4-sulfonyl)-phenylamine, 70 mg (0.5 mmole) 3-thiophen-boronic acid, 55 mg sodium carbonate and 18 mg bis(triphenylphosphine)-palladium(II)-chloride is refluxed for 18 hours in 5 ml 1,2-dimethoxyethane and 0.25 ml water. The solvent is removed and the residue is diluted with dichloromethane. The dichloromethane solution is washed twice with water, dried over magnesiumsulfate and concentrated in vacuo. Flash chromatography (silicagel, ethyl acetate/hexane 1/1) of the residue yields 32 mg (16%) pure 4-(2-pyrrolidine-1-yl-6-thiophen-3-yl-pyridine-4-sulfonyl)-phenylamine as a light brown solid mp.: 260° C.

EXAMPLE 36

4-(2-Naphthalen-1-yl-6-pyrrolidin-1-yl-pyridine-4-sulfonyl)-phenylamine

A mixture of 191 mg (0.5 mmole) 4-(2-bromo-6-pyrrolidine-1-yl-pyridine-4-sulfonyl)-phenylamine, 106 mg (0.55 mmole) 1-naphthylboronic acid, 18 mg bis (triphenylphosphine)-palladium(II)-chloride is refluxed for 20 hours in 7 ml toluene and 2 ml 2N aqueous potassium carbonate. The solvents are removed in vacuo. Flash chromatography (silicagel, ethyl acetate/hexane 1/1) of the residue yields 44 mg (20%) pure 4-(2-naphthalen-1-yl-6-pyrrolidine-1-yl-pyridine-4-sulfonyl)-phenylamine as an amorphous solid with corresponding NMR- and mass spectra.

EXAMPLE 37

4-[2-(1-Methyl-cyclopropyl)-6-pyrrolidin-1-yl-pyridine-4-sulfonyl]-phenylamine 0.164 g (0.00048 Mol) 4-(2-Isopropenyl-6-pyrrolidin-1-yl-pyridine-4-sulfonyl)-phenylamine were dissolved in ethyl ether (100 ml) and cooled to 0° C. A solution of diazomethane in ethyl ether (30 ml) was carefully added. Upon addition of a catalytic amount of $Pd(OAc)_2$ gas evolution started. The reaction mixture was allowed to warm to ambient temperature and stirred for 30 min. After addition of a few drops of acetic acid the solvent was evaporated and the residue chromatographed on $SiO_2$ with ethyl acetate hexane 1:2. It was obtained 0.136 g (71%) of 4-[2-(1-Methyl-cyclopropyl)-6-pyrrolidin-1-yl-pyridine-4-sulfonyl]-phenylamine as pale yellow cristals; mp.: 235–236° C. (dec.).

EXAMPLE 38

4-[2-(2-Fluoro-phenyl)-6-pyrrolidin-1-yl-pyridine-4-sulfonyl]-phenylamine

A mixture of 191 mg (0.5 mmole) 4-(2-bromo-6-pyrrolidine-1-yl-pyridine-4-sulfonyl)-phenylamine, 77 mg (0.55 mmole) 2-fluorophenylboronic acid, 18 mg bis (triphenylphosphine)-palladium(II)-chloride is refluxed for 3 hours in 7 ml toluene and 2 ml 2N aqueous potassium carbonate. The solvents are removed in vacuo. Flash chromatography (silicagel, ethyl acetate/hexane 1/1) of the residue yields 130 mg (65%) pure 4-[2-(2-fluoro-phenyl)-6-pyrrolidine-1-yl-pyridine-4-sulfonyl]-phenylamine as a pale yellow solid mp.: 246–248° C.

EXAMPLE 39

4-(2-Naphthalen-2-yl-6-pyrrolidin-1-yl-pyridine-4-sulfonyl)-phenylamine

A mixture of 191 mg (0.5 mmole) 4-(2-bromo-6-pyrrolidine-1-yl-pyridine-4-sulfonyl)-phenylamine, 95 mg (0.55 mmole) 2-naphthylboronic acid, 18 mg bis (triphenylphosphine)-palladium(II)-chloride is refluxed for 2 hours in 20 ml toluene and 5 ml 2N aqueous potassium carbonate. The solvents are removed in vacuo. Flash chromatography (silicagel, ethyl acetate/hexane 1/1) of the residue yields 76 mg (36%) pure 4-(2-naphthalen-2-yl-6-pyrrolidine-1-yl-pyridine-4-sulfonyl)-phenylamine as a pale yellow solid mp.: 244–246° C.

EXAMPLE 40

4-(2-Bromo-6-piperazin-1-ylpyridine-4-sulphonyl)-phenylamine 0.275 g (0.0007 mol) of 4-(2,6-dibromopyridine-4-sulphonyl)-phenylamine was dissolved in 10 ml of dioxane and treated with 0.066 g (0.00077 mol) of piperazine and 1 ml of triethylamine. The mixture was stirred at 40° C. for 72 hrs. and the solvent was then removed. The residue was partitioned in ethyl acetate and water and the organic phase was extracted with sat. sodium chloride solution and dried over $MgSO_4$ and filtered. After removal of the solvent the residue was chromatographed on silica gel with dichloromethane/methanol 9:1 and there was obtained 0.23 g (82%) of 4-(2-bromo-6-piperazin-1-ylpyridin-4-sulphonyl) -phenylamine as yellowish crystals; m.p.: 173–175° C.

EXAMPLE 41

4-(2-Bromo-6-morpholin-4-ylpyridin-4-sulphonyl)-phenylamine 0.211 g (0.0005 mol) of 4-(2,6-dibromopyridine-4-sulphonyl)-phenylamine was dissolved in 10 ml of dioxane and treated with 0.217 g (0.0025 mol) of morpholine and 1 ml of triethylamine. The mixture was stirred at 40° C for 72 hrs. and the solvent was then removed. The residue was partitioned in ethyl acetate and water and the organic phase was extracted with sat. sodium chloride solution and dried over $MgSO_4$. After removal of the solvent the residue was chromatographed on silica gel with ethyl acetate/hexane 1:1 and there was obtained 0.07 g (35%) of 4(2-bromo-6-morpholine-4-ylpyridine-4-sulphonyl)-phenylamine as white crystals; m.p.: 244–245° C.

EXAMPLE 42

N-[4-(4-Aminobenzenesulphonyl)-6-bromopyridin-2-yl]-N',N'-dimethylethane-1,2diamine 0.098 g (0.00025 mol) of 4-(2,6-dibromopyridine-4-sulphonyl)-phenylamine was dissolved in 3 ml of dioxane and treated with 0.27 ml of 2dimethylaminoethylamine. The mixture was stirred at 60° C. for 48 hrs., the solvent was removed and the residue was chromatographed on silica gel with 2% methanol in dichloromethane. There was obtained 0.084 g (84%) of N-[4-(4-aminobenzenesulphonyl)-6-bromopyridin-2-yl]-N',N'-dimethylethane-1,2-diamine as a light yellow, amorphous solid. MS (ISP): me/e =401, 399 ($C_{15}H_{20}BrN_4O_2S^+$).

EXAMPLE 43

N-[4-(4-Aminobenzenesulphonyl)-6-bromopyridin-2-yl]-N,N',N'-trimethylethane-1,2-diamine 0.118 g (0.0003 mol) of 4-(2,6-dibromopyridine-4-sulphonyl)-phenylamine was dissolved in 5 ml of dioxane and treated with 0.39 ml of N,N,N'-trimethylethylenediamine. The mixture was stirred at room temperature for 20 hrs., the solvent was removed and the residue was chromatographed on silica gel with 5% methanol in dichloromethane. There was obtained 0.123 g (99%) of N-[4-(4-aminobenzenesulphonyl)-6-bromopyridin-2-yl]-N,N',N'-trimethylethane-1,2-diamine as a light yellow, amorphous solid. MS (ISP): me/e=415, 413 ($C_{16}H_{21}BrN_4O_2S^+$).

EXAMPLE 44

[4-(4-Aminobenzenesulphonyl)-6-bromopyridin-2-yl]-(3-morpholin-4-ylpropyl)amine 0.162 g (0.00041 mol) of 4-(2,6-dibrompyridine-4-sulphonyl)-phenylamine was dissolved in 6 ml of dioxane and treated with 0.60 ml of 4-(3-aminopropyl)morpholine. The mixture was stirred at 60° C. for 24 hrs., the solvent was removed and the residue was chromatographed on silica gel with 3% methanol in dichloromethane. There was obtained 0.15 g (80%) of [4-(4-aminobenzenesulphonyl)-6-brompyridin-2-yl]-(3-morpholin-4-ylpropyl)amine as a white, amorphous solid. MS (ISP): me/e=457, 455 ($C_{18}H_{24}BrN_4O_3S^+$).

EXAMPLE 45

N-[3-(4-Aminobenzenesulphonyl)-5-bromphenyl]-N'-methylpropane-1,3-diamine 0.20 g (0.00051 mol) of 4-(2,6-dibromopyridine-4-sulphonyl)-phenylamine was dissolved in 10 ml of dioxane and treated with 5.1 ml of 3-methylaminopropylamine. The mixture was stirred at room temperature for 2 hrs., the solvent was removed and the residue was chromatographed twice on silica gel, firstly with 20% methanol in dichloromethane and then with 10% methanol in dichloromethane. There was obtained 0.085 g (42%) of N-[3-(4-aminobenzenesulphonyl)-5-bromophenyl]-N'-methylpropane-1,3-diamine as a pale yellow, amorphous solid; MS (ISP): me/e=401, 399 ($C_{15}H_{20}BrN_4O_2S^+$).

EXAMPLE 46

N-[4-(4-Aminobenzolsulphonyl)-6-bromopyridin-2-yl]-N',N'-dimethylpropane-1,3-diamine 0.16 g (0.00041 mol) of 4-(2,6-dibromopyridine-4-sulphonyl)-phenylamine was dissolved in 6 ml of dioxane and treated with 0.52 ml of 3-dimethylamino-1propylamine. The mixture was stirred at 60° C. for 24 hrs., the solvent was removed and the residue was chromatographed on silica gel firstly with 5% methanol in dichloromethane and then with 10% methanol in dichloromethane. The product-containing fractions were freed from solvent, the residue was dissolved in 1N HCl, filtered and the filtrate was adjusted to pH 9 with 1N NaOH. The precipitate which thereby resulted was filtered off under suction and dried in a high vacuum. There was obtained 0.072 g (43%) of N-[4-(4-aminobenzenesulphonyl)-6-bromopyridin-2-yl]-N',N'-dimethylpropane-1,3-diamine as pink coloured crystals; m.p.: >250° C. (dec.).

EXAMPLE 47

N-[4-(4-Aminobenzenesulphonyl)-6-bromopyridin-2-yl]-N',N'-diethylpropane-1,3-diamine 0.20 g (0.00051 mol) of 4-(2,6-dibromopyridine-4-sulphonyl)-phenylamine was dissolved in 10 ml of dioxane and treated with 8.0 ml of 3-diethylamino-1propylamine. The mixture was stirred at room temperature for 18 hrs., the solvent was removed and the residue was chromatographed twice on silica gel, firstly with 20% methanol in dichloromethane and then with 10% methanol in dichloromethane. There was obtained 0.09 g (41%) of N-[4-(4-aminobenzenesulphonyl)-6-bromopyridin-2-yl]-N',N'-diethylpropane-1,3-diamine as a pale yellow, amorphous solid. MS (ISP): me/e=443, 441 ($C_{18}H_{26}BrN_4O_2S^+$).

EXAMPLE 48

3-[3-(4-Aminobenzenesulphonyl)-5-bromophenylamino]-propan-1-ol 0.20 g (0.00051 mol) of 4-(2,6-dibromopyridine-4-sulphonyl)-phenylamine was dissolved in 10 ml dioxane and treated with 3.8 ml of 3-amino-1-propanol. The mixture was stirred at room temperature for 18 hrs., the solvent was removed and the residue was chromatographed on silica gel with ethyl acetate/hexane 1:1 and finally with pure ethyl acetate. There was obtained 0.158 g (80%) of 3-[3-(4-aminobenzenesulphonyl)-5-bromophenylamino]-propan-1-ol as a brownish oil. MS (ISP): me/e=388, 386 ($C_{14}H_{17}BrN_3O_3S^+$).

EXAMPLE 49

N1-[4-(4-Aminobenzenesulphonyl)-6-bromopyridin-2-yl]-butane-1,4-diamine 0.39 g (0.001 mol) of 4-(2,6-dibromopyridine-4-sulphonyl)-phenylamine was dissolved in 10 ml of dioxane and treated with 1.9 ml (0.01 mol) of N-tert.-butoxycarbonyl-1,4-diaminobutane. The mixture was stirred at 60° C. for 18 hrs., the solvent was removed and the residue was chromatographed on silica gel with ethyl acetate/hexane 1:1. There was obtained 0.36 g (77%) of tert-butyl [4-[4-(4-aminobenzenesulphonyl)-6-bromopyridin-2-ylamino]-butyl]-carbamate as a pale yellow oil. MS (ISP): me/e=501, 499 ($C_{20}H_{26}BrN_4O_4S^+$).

0.36 g (0.00072 mol) of tert-butyl [4-[4-(4-aminobenzenesulphonyl)-6-bromopyridin-2-ylamino]-butyl]-carbamate was dissolved in 15 ml of dioxane and treated with 5 ml of 3N aqueous HCl. After stirring at room temperature for 18 hrs. the pH was adjusted to 9, the reaction mixture was extracted with ethyl acetate and the organic phase was washed with water and sat. sodium chloride solution, dried over $MgSO_4$ and concentrated. The residue was chromatographed on silica gel with 10% methanol in dichloromethane and then with 20% methanol in dichloromethane. After removal of the solvent from the product-containing fractions the residue was dissolved in diethyl ether and the product was precipitated by the addition of hexane. There was obtained 0.03 g (10%) of N1-[4 -(4-aminobenzenesulphonyl)-6-bromopyridin-2-yl]-butane-1,4-diamine as orange-red crystals. MS (ISP): me/e=401, 399 ($C_{15}H_{20}BrN_4O_2S^+$).

EXAMPLE 50

[6-Bromo-4-(3-trifluoromethylbenzenesulphonyl)-pyridin-2-yl]-methylamine 1.0 g (0.0056 mol) of 3-trifluoromethylthiophenol was dissolved in 17 ml of dimethylformamide and treated with 0.64 g (0.0056 mol) of potassium tert.-butylate. The mixture was stirred at room temperature for 20 min. and then treated with 1.58 g (0.0056 mol) of 2,6-dibromo-4-nitro-pyridine. The mixture was stirred at room temperature for 3 hrs., the solvent was then removed and the residue was partitioned in water and ethyl acetate. The organic phase was washed with sat. sodium chloride solution, dried over $MgSO_4$, filtered and, after removal of the solvent, the residue was chromatographed on silica gel with ethyl acetate/hexane 1:39. There was obtained 2.08 g (90%) of 2,6-dibromo-4-(3-trifluoromethylphenylsulphanyl)-pyridine as yellow crystals; m.p.: 68–70° C.

2.0 g (0.0049 mol) of 2,6-dibromo-4-(3-trifluoromethylphenylsulphanyl)-pyridine were dissolved in 200 ml of dichloromethane and treated with 8.05 g (0.0323 mol) of meta-chloroperbenzoic acid (70%). The mixture was stirred at room temperature for 72 hrs. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:19. There were obtained 1.74 g (80%) of 2,6-dibromo-4-(3-trifluoromethylbenzenesulphonyl)-pyridine as white crystals; m.p.: 156–158° C.

0.222 g (0.0005 mol) of 2,6-dibromo-4-(3-trifluoromethylbenzenesulphonyl)-pyridine was dissolved in 10 ml of dioxane and treated with 1.25 ml of 8M methylamine in ethanol. The mixture was stirred at room temperature for 18 mins., the solvents were then removed and the residue was chromatographed on silica gel with ethyl acetate/hexane 1:19 and subsequently 1:9. There was obtained 0.16 g (81%) of [6-bromo-4-(3-trifluoromethylbenzenesulphonyl) -pyridin-2-yl]-methylamine as yellow crystals; m.p.: 115–117° C.

EXAMPLE 51

[6-Bromo-4-(3-trifluoromethylbenzenesulphonyl)-pyridin-2-yl]-dimethylamine 0.222 g (0.0005 mol) of 2,6-dibromo-4-(3-trifluoromethylbenzenesulphonyl)-pyridine was dissolved in 10 ml of dioxane and treated with 0.89 ml of 5.6M dimethylamine in ethanol. The mixture was stirred at room temperature for 1.5 hrs., the solvents were then removed and the residue was chromatographed on silica gel with ethyl acetate/hexane 1:9. There was obtained 0.18 g (88%) of 6-bromo-4-(3-trifluoromethylbenzenesulphonyl)-pyridin-2-yl]-dimethylamine as yellow crystals; m.p.: 117–118° C.

EXAMPLE 52

1-[6-Bromo-4-(3-trifluoromethylbenzenesulphonyl)-pyridin-2-yl]-piperazine 0.222 g (0.0005 mol) of 2,6-dibromo-4-(3-trifluoromethylbenzenesulphonyl)-pyridine was dissolved in 10 ml of dioxan and treated with 0.047 g (0.00055 mol) of piperazine and 0.7 ml of triethylamine. The mixture was stirred at room temperature for 20 hrs. and subsequently at 40° C. for 3 hrs., the solvent was then removed and the residue was chromatographed on silica gel with 5% methanol in dichloromethane. There was obtained 0.14 g (62%) of 1-[6-bromo-4-(3-trifluoromethylbenzenesulphonyl)-pyridin-2-yl]-piperazine as yellow crystals; m.p.: 160–162° C.

EXAMPLE 53

[6-Bromo-4-(naphthyl-2-sulphonyl)-pyridin-2-yl]-methylamine 0.085 g (0.0003 mol) of 2,6-dibromo-4-nitropyridine was dissolved in 3 ml of dimethylformamide and treated with 0.065 g (0.0003 mol) of 2-naphthylsulphinic acid sodium salt. The mixture was stirred at 50° C. for 1 hr., the solvent was distilled off and the residue was partitioned in water and ethyl acetate. The organic phase was washed with sat. sodium chloride solution, dried over $MgSO_4$, filtered and, after removal of the solvent, the residue was chromatographed on silica gel with ethyl acetate/hexane 1:19. There was obtained 0.085 g (66%) of 2,6-dibromo-4-(naphthyl-2-sulphonyl)-pyridine as white crystals; m.p.: 178–179° C.

0.07 g (0.00016 mol) of 2,6-dibromo-4-(naphthyl-2-sulphonyl)-pyridine was dissolved in 6 ml of dioxane and treated with 1 ml of 8 M methylamine in ethanol. The mixture was stirred at room temperature for 48 hrs., the solvents were removed and the residue was chromatographed on silica gel with ethyl acetate/hexane 1:7. There was obtained 0.049 g (79%) of [6-bromo-4-(naphthyl-2-sulphonyl)-pyridin-2-yl]-methylamine as white crystals; m.p.: 149–151° C.

EXAMPLE 54

[6-Bromo-4-(naphthyl-1-sulphonyl)-pyridin-2-yl]-methylamine 0.564 g (0.002 mol) of 2,6-dibromo-4-nitropyridine was dissolved in 20 ml of dimethylformamide and treated with 0.45 g (0.0021 mol) of 1-naphthylsulphinic acid sodium salt. The mixture was stirred at 50° C. for 2 hrs., the solvent was distilled off and the residue was partitioned in water and ethyl acetate. The organic phase was washed with sat. sodium chloride solution, dried over $MgSO_4$, filtered and, after removal of the solvent, the residue was chromatographed on silica gel with ethyl acetate/hexane 1:19. There was obtained 0.46 g (54%) of 2,6-dibromo-4-(naphthyl-1-sulphonyl)-pyridine as brown crystals; m.p.: 140–142° C.

0.21 g (0.0005 mol) of 2,6-dibromo-4-(naphthyl-1-sulphonyl)-pyridine was dissolved in 10 ml of dioxane and treated with 0.63 ml of 8 M methylamine in ethanol. The mixture was stirred at room temperature for 24 hrs., the solvents were removed and the residue was chromatographed on silica gel with ethyl acetate/hexane 1:19. There was obtained 0.13 g (69%) of [6-bromo-4-(naphthyl-1-sulphonyl)-pyridin-2-yl]-methylamine as yellowish crystals; m.p.: 162–164° C.

EXAMPLE 55

[3-Bromo-5-(naphthyl-1-sulphonyl)-phenyl]-dimethylamine 0.185 g (0.00043 mol) of 2,6-dibromo-4-(naphthyl-1-sulphonyl)-pyridine was dissolved in 8 ml of dioxane and treated with 0.77 ml of 5.6M dimethylamine in ethanol. The mixture was stirred at room temperature for 6 hrs., the solvents were removed and the residue was chromatographed on silica gel with ethyl acetate/hexane 1:9. There was obtained 0.16 g (94%) of [3-bromo-5-(naphthyl-1-sulphonyl)-phenyl]-dimethylamine as yellow crystals; m.p.: 158–160° C.

EXAMPLE 56

2-(4-Aminobenzenesulphonyl)-6-bromopyridin-4-ylamine 19.7 g (0.0699 mol) of 2,6-dibromo-4-nitropyridine and 13.5 g (0.0699 mol) of 4-nitrothiophenol potassium salt were dissolved in 350 ml of dimethylformamide and stirred at room temperature for 18 hrs. The solvent was removed and the residue was partitioned in water and dichloromethane. The combined organic phases were washed with sat. sodium chloride solution and dried over $MgSO_4$. After filtration and removal of the solvent the residue was chromatographed on silica gel with dichloromethane and subsequently dried in a high vacuum. There were obtained 23.6 g of a mixture of 2,6-dibromo-4-(4-nitrophenylsulphanyl)-pyridine and 2-bromo-4-nitro-6-(4-nitrophenylsulphanyl)-pyridine, which was dissolved in 0.5 l of dichloromethane and treated with 33.0 g (0.134 mol) of meta-chloroperbenzoic acid (70%). The mixture was stirred at room temperature for 2 hrs. Subsequently, the reaction mixture was extracted with sat. $Na_2CO_3$ solution and sat. sodium chloride solution, dried over $MgSO_4$ and, after filtration and removal of the solvent, chromatographed on silica gel with dichloromethane/hexane 1:1 and 2:1. There were obtained 22.30 g (87%) of 2,6-dibromo-4-(4-nitrobenzenesulphonyl)-pyridine as a first fraction and 0.55 g (2.4%) of 2-bromo-4nitro-6-(4-nitrobenzenesulphonyl)-pyridine as yellowish crystals in the second fraction; m.p.: 154–156° C.

0.10 g (0.00026 mol) of 2-bromo-4-nitro-6-(4-nitrobenzenesulphonyl)-pyridine was dissolved in a mixture of 1.5 ml of methanol and 1.5 ml of dioxane, treated with 0.20 g of iron powder and a solution of 0.20 g of $NH_4Cl$ in 2.5 ml of water and heated at reflux for 2 hrs. Thereafter, the reaction mixture was poured into a mixture of ethyl acetate and water, suction filtered and the organic phase was extracted with water and sat. sodium chloride solution and dried over $MgSO_4$. After removal of the solvent the residue was chromatographed on silica gel with ethyl acetate/hexane 1:4. There was obtained 0.037 g (44%) of 2-(4-aminobenzenesulphonyl)-6-bromopyridin-4-ylamine as yellowish crystals; m.p.: 202–204° C.

EXAMPLE 57

[2-(4-Aminobenzenesulphonyl)-6-bromopyridin-4-yl]-methylamine 0.10 g (0.00026 mol) of 2-bromo-4-nitro-6-(4-nitrobenzenesulphonyl)-pyridine was dissolved in 3.2 ml of dioxane and treated with 3.2 ml of 8M methylamine in ethanol. The mixture was stirred at room temperature for 3 hrs., the solvents were removed and the residue was chromatographed on silica gel with ethyl acetate/hexane 1:4. There was obtained 0.065 g (68%) of [2-bromo-6-(4-nitrobenzenesulphonyl)-pyridin-4-yl]-methylamine as pale yellow crystals; m.p.: 191–192° C.

0.078 g (0.00021 mol) of [2-bromo-6-(4-nitrobenzenesulphonyl) -pyridin-4-yl]-methylamine was dissolved in a mixture of 1.5 ml of methanol and 1.5 ml of dioxane, treated with 0.078 g of iron powder and a solution of 0.078 g of $NH_4Cl$ in 2.5 ml of water and heated at reflux for 2 hrs. Therafter, the reaction mixture was poured into a mixture of ethyl acetate and water, suction filtered and the organic phase was extracted with water and sat. sodium chloride solution and dried over $MgSO_4$. After removal of the solvent the residue was chromatographed on silical gel with ethyl acetate/hexane 1:3. There was obtained 0.063 g (88%) of [2-(4-aminobenzenesulphonyl)-6-bromopyridin-4-yl]-methylamine as yellowish crystals; m.p.: 158–160° C.

EXAMPLE 58

4-(2-Bromo-6-methylpyridine-4-sulphonyl)-phenylamine 1.0 g (0.00458 mol) of 2-bromo-6-methyl-4-nitropyridine and 0.885 g (0.00458 mol) of 4-nitrothiophenol potassium salt were dissolved in 10 ml of 1-methyl-pyrrolidone and stirred at 50° C. for 1 hr. The solvent was removed in a high vacuum and the residue was partitioned in water and ethyl acetate. The combined organic phases were washed with sat. sodium chloride solution and dried over $MgSO_4$. After filtration and removal of the solvent the residue was chromatographed on silica gel with ethyl acetate/hexane 1:4 and 1:3 and subsequently dried in a high vacuum. There was obtained 0.945 g (63%) of 2-bromo-6-methyl-4-(4-nitrophenylsulphanyl)-pyridine as yellow crystals; m.p.: 124–126° C.

0.50 g (0.0015 mol) of 2-bromo-6-methyl-4-(4-nitrophenylsulphanyl)-pyridine was dissolved in 20 ml of dichloromethane and treated with 0.865 g (0.0034 mol) of meta-chloroperbenzoic acid (70%). The mixture was stirred at room temperature for 3 hrs. Subsequently, the reaction mixture was extracted with sat. $Na_2CO_3$ solution and sat. sodium chloride solution, dried over $MgSO_4$ and, after filtration and removal of the solvent, chromatographed on silica gel with ethyl acetate/hexane 1:9. There was obtained 0.53 g (96%) of 2-bromo-6-methyl-4-(4-nitrobenzenesulphonyl)-pyridine as yellowish crystals; m.p.: 154–156 ° C.

0.15 g (0.00042 mol) of 2-bromo-6-methyl-4-(4-nitrobenzenesulphonyl)-pyridine was dissolved in 10 ml of methanol, treated with 0.18 g of iron powder and a solution of 0.18 g of $NH_4Cl$ in 5 ml of water and heated at reflux for 1 hr. Thereafter, the reaction mixture was poured into a mixture of ethyl acetate and water, suction filtered and the organic phase was extracted with water and sat. sodium chloride solution and dried over $MgSO_4$. After removal of the solvent the residue was dried in a high vacuum. There was obtained 0.134 g (98%) of 4-(2-bromo-6-methylpyridine-4-sulphonyl)-phenylamine as yellowish crystals; m.p.: 189–191° C.

EXAMPLE 59

[4-(4-Aminobenzenesulphonyl)-6-methylpyridin-2-yl]-methylamine 0.056 g (0.00017 mol) of 4-(2-bromo-6-methylpyridine-4-sulphonyl)-phenylamine and 1.1 ml of 8 M methylamine in ethanol were stirred at 120° C. in 5 ml of dioxane for 24 hrs. After removal of the solvent the residue was chromatographed on silica gel with ethyl acetate/hexane 1:1. The product-containing fraction were suspended in 25 ml of diethyl ether, treated in an ultrasound bath and diluted with 45 ml of hexane. The suspension was suction filtered and the filter material was dried in a high vacuum. There was obtained 0.04 g (84%) of [4-(4-aminobenzenesulphonyl)-6-methyl-pyridin-2-yl]-methylamine as light yellow crystals; m.p.: 126–127° C.

EXAMPLE 60

[4-(4-Aminobenzenesulphonyl)-6-methylpyridin-2-yl]-dimethylamine 0.13 g (0.0004 mol) of 4-(2-bromo-6-methylpyridine-4-sulphonyl)-phenylamine and 5.0 ml of 5.6 M methylamine in ethanol were stirred at 60° C. in 20 ml of dioxane for 24 hrs. After removal of the solvents the residue was chromatographed on silica gel with ethyl acetate/hexane 1:2. The product-containing fractions were suspended in 25 ml of diethyl ether, treated in an ultrasound bath and diluted with 45 ml of hexane. The suspension was suction filtered and the filter material was dried in a high vacuum. There was obtained 0.10 g (86%) of [4-(4-aminobenzenesulphonyl)-6-methyl-pyridin-2-yl]-dimethylamine as white crystals; m.p.: 157–159° C.

EXAMPLE 61

4-(3,5-Dimethylbenzenesulphonyl)-phenylamine 0.25 g (0.0014 mol) of 3,5-dimethylthiophenol potassium salt were dissolved in 5 ml of 1-methyl-2-pyrrolidone, treated with 0.19 g (0.00134 mol) of 1-fluoro-4-nitrobenzene and a spatula tip of Cu powder and stirred at 160° C. for about 5 hrs. Thereafter, the solvent was removed by distillation, the residue was partitioned in water/ethyl acetate and the organic phase was washed with sat. sodium chloride solution and dried over $MgSO_4$. After filtration and removal of the solvent the residue was chromatographed on silica gel with ethyl acetate/hexane 1:15. There was obtained 0.22 g (62%) of 1,3-dimethyl-5-(4-nitrophenylsulphanyl)-benzene as a viscous, yellow oil. MS (EI): me/e=259 ($C_{14}H_{13}NO_2S^+$).

0.215 g (0.00083 mol) of 1,3-dimethyl-5-(4-nitrophenylsulphanyl)-benzene was dissolved in 25 ml of dichloromethane and treated with 0.56 g (0.0018 mol) of meta-chloroperbenzoic acid (55%). The mixture was stirred at room temperature for 4 hrs. Then, the reaction mixture was extracted with sat. $Na_2CO_3$ solution and with sat. sodium chloride solution. After drying over $MgSO_4$, filtration and removal of the solvent there was obtained 0.276 g (100%) of 1,3-dimethyl-5-(4-nitrobenzenesulphonyl)-benzene as beige crystals; m.p.: 179–180° C.

0.27 g (0.0009 mol) of 1,3-dimethyl-5-(4-nitrobenzenesulphonyl)-benzene was suspended in 40 ml of ethanol, treated with 0.03 g of Pd/C (10%) and stirred in a $H_2$ atmosphere at room temperature under normal pressure for 2 hrs. Then, the catalyst was filtered off, the filtrate was freed from solvent and the residue was chromatographed on silica gel with ethyl acetate/hexane 2:1. There was obtained 0.157 g (73%) of 4-(3,5-dimethylbenzenesulphonyl)-phenylamine as white crystals; m.p.: 178–179° C.

EXAMPLE 62

4-(3.5-Dimethoxy-benzenesulphonyl)-phenylamine 0.30 g (0.00144 mol) of 3,5-dimethoxythiophenol potassium salt was dissolved in 5 ml of 1-methyl-2-pyrrolidone, treated with 0.21 g (0.00144 mol) of 1-fluoro-4-nitrobenzene and a spatula tip of Cu powder and stirred at 160° C. for about 3 hrs. Thereafter, the solvent was removed by distillation, the residue was partitioned in water/ethyl acetate and the organic phase was washed with sat. sodium chloride solution and dried over $MgSO_4$. After filtration and removal of the solvent the residue was chromatographed on silica gel with ethyl acetate/hexane 1:7. There was obtained 0.255 g (60%) of 1,3-dimethoxy-5-(4-nitrophenylsulphanyl)-benzene as yellow crystals; m.p.: 63–65° C.

0.245 g (0.00084 mol) of 1,3-dimethoxy-5-(4-nitrophenylsulphanyl)-benzene was dissolved in 20 ml of dichloromethane and treated with 0.455 g (0.0018 mol) of meta-chloroperbenzoic acid (70%). The mixture was stirred at room temperature for 4 hrs. Then, the reaction mixture was extracted with sat. $Na_2CO_3$ solution and with sat. sodium chloride solution. After drying over $MgSO_4$, filtration and removal of the solvent there was obtained 0.22 g (81%) of 1,3-dimethoxy-5-(4-nitrophenylsulphonyl)-benzene as white crystals; m.p.: 150–152° C.

0.22 g (0.00068 mol) of 1,3-dimethoxy-5-(4-nitrophenylsulphonyl)-benzene was suspended in a mixture of 15 ml of methanol and 7.5 ml of water, treated with 0.30 g of iron powder and 0.30 g of $NH_4Cl$ and heated at reflux for 1 hr. After cooling the mixture was diluted with 50 ml of methanol, treated in an ultrasound bath for a short time and suction filtered. The filter material was washed with a large amount of methanol and the filtrate was concentrated. The residue was suspended in water and treated in an ultrasound bath. The precipitate which thereby resulted was filtered off under suction and dried in a high vacuum. There was obtained 0.18 g (90%) of 4-(3,5-dimethoxybenzenesulphonyl)-phenylamine as white crystals; m.p.: 128–130° C.

EXAMPLE 63

4-(3,5-Dimethoxybenzenesulphonyl)-2-methylphenylamine 0.426 g (0.0021 mol) of 3,5-dimethoxythiophenol potassium salt was dissolved in 7 ml of 1-methyl-2-pyrrolidone, treated with 0.317 g (0.0021 mol) of 5-fluoro-2-nitrotoluene and a spatula tip of Cu powder and stirred at 160° C. for about 5 hrs. Thereafter, the reaction mixture was partitioned in water/diethyl ether and the organic phase was washed with sat. sodium chloride solution and dried over $MgSO_4$. After filtration and removal of the solvent the residue was chromatographed on silica gel with ethyl acetate/hexane 1:9. There was obtained 0.343 g (55%) of 1-(3,5-dimethoxyphenylsulphanyl)-3-methyl-4-nitrobenzene as a yellow oil. MS (EI): me/e=305 ($C_{15}H_{15}NO_4S^+$).

0.317 g (0.00104 mol) of 1-(3,5-dimethoxyphenylsulphanyl)-3-methyl-4nitrobenzene was dissolved in 40 ml of dichloromethane and treated with 0.563 g (0.00228 mol) of meta-chloroperbenzoic acid (70%). The mixture was stirred at room temperature for 1.5 hrs. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:4. There was obtained 0.31 g (87%) of 1-(3,5dimethoxyphenylsulphonyl)-3-methyl-4-nitrobenzene as yellowish crystals; m.p.: 125–127° C.

0.29 g (0.00086 mol) of 1-(3,5-dimethoxyphenylsulphonyl)-3-methyl-4-nitrobenzene was suspended in a mixture of 10 ml of methanol and 10 ml of water, treated with 0.30 g of iron powder and 0.30 g of $NH_4Cl$ and heated at reflux for 1.5 hrs. After cooling the mixture was diluted with 50 ml of methanol, treated in an ultrasound bath for a short time and suction filtered. The filter material was washed with a large amount of methanol and the filtrate was concentrated. The residue was suspended in water and treated in an ultrasound bath. The precipitate which thereby resulted was filtered off under suction and chromatographed on silica gel with ethyl acetate/hexane 1:1. There was obtained 0.246 g (92.5%) of 4-(3,5-dimethoxybenzenesulphonyl)-2-methyl-phenylamine as yellow coloured crystals; m.p.: 121–123° C.

EXAMPLE 64

(3-Benzenesulphonyl-5-bromophenyl)-methylamine 28.40 g (0.131 mol) of 3-bromo-5-nitroaniline were dissolved in 250 ml of pyridine and treated with 30 ml (0.317 mol) of acetic anhydride. The mixture was stirred at room temperature for 18 hrs. and subsequently at 40° C. for 2 hrs. Then, the residue was digested in water and the precipitate was filtered off. The filter material was rinsed with a large amount of water and dried at 45° C. in a high vacuum. There were obtained 31.0 g (91.5%) of N-(3-bromo-5-nitrophenyl)-acetamide as orange-yellow crystals. MS (ISP): me/e=260, 258 ($C_8H_8BrN_2O_3^+$).

31.0 g (0.1197 mol) of N-(3-bromo-5-nitrophenyl)-acetamide were dissolved in 240 ml of dimethylformamide and added dropwise within 20 min. to a suspension, cooled at 5° C., of 5.8 g (0.1325 mol) of NaH (60%) in 120 ml of dimethylformamide. Subsequently, the mixture was stirred at room temperature for 1 hr., again cooled to 0–5° C. and 22.30 ml (0.358 mol) of MeI were added thereto. The mixture was stirred at room temperature for 18 hrs., then freed from solvent and the residue was partitioned in water and dichloromethane. The organic phase was washed with sat. sodium chloride solution, dried over $MgSO_4$, filtered and concentrated. The residue was chromatographed on silica gel with ethyl acetate/hexane. There were obtained 29.0 g (88.7%) of N-(3-bromo-5-nitrophenyl)-N-methylacetamide as a brown oil. MS (El): me/e=274,272 ($C_9H_9BrN_2O_3^+$).

4.5 g (0.0165 mol) of N-(3-bromo-5-nitrophenyl)-N-methylacetamide were dissolved in 75 ml of ethanol, treated while cooling with a solution of 15.0 g (0.0665 mol) of $SnCl_2.2H_2O$ in 30 ml of HCl (37%) and stirred at room temperature for 18 hrs. Then, the solvent was removed, the residue was adjusted to pH 8 with sat. $NaHCO_3$ solution, extracted with ethyl acetate and sat. sodium chloride solution and the organic phase was dried over $MgSO_4$, filtered and concentrated. The residue was chromatographed on silica gel with ethyl acetate/hexane 1:2, 1:1 and finally 2:1. There were obtained 2.35 g (59%) of N-(3-amino-5-bromophenyl)-N-methylacetamide as light brown crystals. MS (EI): me/e=244,242 ($C_9H_{11}BrN_2O^+$).

0.243 g (0.001 mol) of N-(3-amino-5-bromophenyl)-N-methylacetamide was suspended in 5 ml of water, treated with 0.2 ml (0.002 mol) of HCl (37%) and cooled to 0° C. A solution of 0.069 g (0.001 mol) of $NaNO_2$ in 1 ml of water was added thereto, the mixture was stirred at 0° C. for 5 min. and subsequently at room temperature for 10 min. and finally treated with a suspension of 0.35 g (0.0025 mol) of thiophenol sodium salt. The reaction mixture was treated in an ultrasound bath for 10 min. and subsequently partitioned in water/ethyl acetate. The organic phase was washed with sat. sodium chloride solution, dried over $MgSO_4$ filtered and freed from solvent. The residue was then heated to 120–130° C. for 20 min., taken up in ethyl acetate and chromatographed on silica gel with ethyl acetate/hexane 1:9 and 1:2. There was obtained 0.085 g (21%) of N-(3-bromo-5-phenylsulphanylphenyl)-N-methylacetamide as a yellow oil. MS (EI): me/e=337, 335 ($C_{15}H_{14}BrNOS^+$).

0.13 g (0.0004 mol) of N-(3-bromo-5-phenylsulphanylphenyl)-N-methylacetamide was dissolved in 8 ml of dichloromethane and treated with 0.21 g (0.0018 mol) of meta-chloroperbenzoic acid (70%). The mixture was stirred at room temperature for 1 hr. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:2 and 1:1. There was obtained 0.105 g (80%) of N-(3-benzenesulphonyl-5-bromophenyl)-N-methylacetamide as white crystals; m.p.: 147–148° C.

0.10 g (0.000275 mol) of N-(3-benzenesulphonyl-5-bromophenyl)-N-methylacetamide was dissolved in a mixture of 5.5 ml of dioxane and 5.5 ml of 1N NaOH and heated at reflux for 1 hr. Subsequently, the organic solvent was distilled off and the residue was made neutral with 1N HCl and extracted with ethyl acetate. The organic phase was washed with water and sat. sodium chloride solution, dried over $MgSO_4$, filtered and concentrated. The residue was chromatographed on silica gel with ethyl acetate/hexane 1:2. There was obtained 0.86 g (96%) of (3-benzenesulphonyl-5-bromophenyl)-methylamine as a pale yellow solid; m.p.: 143–145° C.

EXAMPLE 65

[3-(4-Aminobenzenesulphonyl)-phenyl]-methylamine 0.265 g (0.00657 mol) of NaH (60%) was suspended in 10 ml of dimethylformamide and treated while cooling with ice with a solution of 1.72 g (0.06 mol) of N-[3-(4-nitrophenylsulphanyl)-phenyl]-acetamide in 20 ml of dimethylformamide. After a few minutes the mixture was left to warm to room temperature and stirred for 1 hr. Then, 1.1 ml (0.0179 mol) of MeI were added slowly. The mixture was stirred at room temperature for 18 hrs., the solvent was thereafter removed and the residue was partitioned in water and ethyl acetate. The organic phase was washed with sat. sodium chloride solution, dried over $MgSO_4$ and concentrated. The residue was chromatographed on silica gel with ethyl acetate/hexane 1:1. There were obtained 1.51 g (83%) of N-methyl-N-[3-(4-nitrophenylsulphanyl)-phenyl]-acetamide as yellow crystals; m.p.: 66–68° C.

1.51 g (0.0050 mol) of N-methyl-N-[3-(4-nitrophenylsulphanyl)-phenyl]acetamide were dissolved in 40 ml of dichloromethane and treated with 2.70 g (0.011 mol) of meta-chloroperbenzoic acid (70%). The mixture was stirred at room temperature for 2 hrs. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:1. There were obtained 1.50 g (90%) of N-methyl-N-[3-(4-nitrobenzenesulphonyl)-phenyl]-acetamide as white crystals; m.p.: 194–195° C.

1.50 g (0.00448 mol) of N-methyl-N-[3-(4-nitrobenzenesulphonyl)-phenyl]-acetamide were suspended in 150 ml of ethanol, treated with 0.15 g of Pd/C (10%) and stirred in a $H_2$ atmosphere at room temperature under normal pressure for 2 hrs. Then, the catalyst was filtered off, the filtrate was freed from solvent and the residue was chromatographed on silica gel with ethyl acetate/hexane 2:1.

There were obtained 1.19 g (87%) of N-[3-(4-amino-benzenesulphonyl)-phenyl]-N-methyl-acetamide as white crystals; m.p.: 178–180° C.

1.19 g (0.0039 mol) of N-[3-(4-amino-benzenesulphonyl)-phenyl]-N-methyl-acetamide were dissolved in a mixture of 70 ml of dioxane and 70 ml of 1N NaOH and heated at reflux for 5 hrs. Subsequently, the organic solvent was distilled off and the residue was made neutral with 1N HCl and extracted with ethyl acetate. The organic phase was washed with water and sat. sodium chloride solution, dried over $MgSO_4$, filtered and concentrated. The residue was chromatographed on silica gel with ethyl acetate/hexane 1:1. The solvent was removed from the product-containing fractions and the residue was recrystallized from ethyl acetate/ether. There was obtained 0.63 g (62%) of [3-(4-amino-benzenesulphonyl) -phenyl]-methylamine as yellow crystals; m.p.: 125–126° C.

EXAMPLE 66

[3-(4-Aminobenzenesulphonyl)-5-bromophenyl]-methylamine 0.243 g (0.001 mol) of N-(3-amino-5-bromophenyl)-N-methylacetamide was suspended in 5 ml of water, treated with 0.2 ml (0.002 mol) of HCl (37%) and cooled to 0° C. A solution of 0.069 g (0.001 mol) of $NaNO_2$ in 1 ml of water was added thereto, the mixture was stirred at 0° C. for 5 min. and subsequently at room temperature for 10 min. and finally treated with a solution of 0.25 g (0.0015 mol) of benzenesulphinic acid sodium salt in 5 ml of water. The reaction mixture was treated in an ultrasound bath for 10 min. and subsequently partitioned in water/ethyl acetate. The organic phase was washed with sat. sodium chloride solution, dried over $MgSO_4$, filtered and freed from solvent. The residue was chromatographed on silica gel with 1% MeOH in dichloromethane. There was obtained 0.23 g (58%) of N-[3-[2-(phenylsulphonyl)-diazenyl]-5-bromophenyl]-N-methylacetamide as a brown oil. MS (ISN): me/e=456, 454 ($C_{15}H_{14}BrN_3O_3S^-$+NaOAc).

0.22 g (0.00055 mol) of N-[3-[2-(phenylsulphonyl)-diazenyl]-5-bromophenyl]-N-methylacetamide was dissolved in 15 ml of dimethyl sulphoxide, treated with 0.185 g (0.000825 mol) of 4-nitrothiophenol potassium salt and stirred at 40° C. for 18 hrs. The reaction mixture was poured into 300 ml of water, extracted with diethyl ether, the organic phase was washed with water and sat. sodium chloride solution, dried over $MgSO_4$, filtered and the filtrate was freed from solvent. The residue was chromatographed on silica gel with 1% MeOH in dichloromethane. There was obtained 0.217 g (100%) of N-[3-bromo-5-(4-nitrophenylsulphanyl)-phenyl]-N-methylacetamide as a yellow oil. MS (EI): me/e=382, 380 ($C_{15}H_{13}BrN_2O_3S^+$).

0.064 g (0.00016 mol) of N-[3-bromo-5-(4-nitrophenylsulphanyl) -phenyl]-N-methylacetamide was dissolved in 20 ml of dichloromethane and treated with 0.09 g (0.00035 mol) of meta-chloroperbenzoic acid (70%). The mixture was stirred at room temperature for 3 hrs. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:1. There was obtained 0.04 g (61%) of N-[3-bromo-5-(4-nitrobenzenesulphonyl)-phenyl]-N-methylacetamide as an amorphous, colourless solid. MS (EI): me/e=414, 412 ($C_{15}H_{13}BrN_2O_5S^+$).

0.04 g (0.00009 mol) of N-[3-bromo-5-(4-nitrobenzenesulphonyl) -phenyl]-N-methylacetamide was dissolved in 5 ml of ethanol, treated while cooling with a solution of 0.085 g (0.00045 mol) of $SnCl_2.2H_2O$ in 0.34 ml of HCl (37%) and stirred at room temperature for 18 hrs. Then, the solvent was removed and the residue was adjusted to pH 8 with sat. $NaHCO_3$ solution. The aqueous phase was extracted with ethyl acetate and the organic phase was washed with sat. sodium chloride solution, dried over $MgSO_4$, filtered and freed from solvent. There was obtained 0.021 g (61%) of N-[3-bromo-5-(4-aminobenzenesulphonyl)-phenyl]-N-methylacetamide as a light yellow oil. MS (ISN): me/e=443, 441 ($C_{15}H_{15}BrN_2O_3S^-$+NaOAc).

0.021 g (0.000054 mol) of N-[3-bromo-5-(4-aminobenzenesulphonyl)-phenyl]-N-methylacetamide was dissolved in a mixture of 10 ml of dioxane and 10 ml of 1N NaOH and heated at reflux for 2 hrs. Subsequently, the organic solvent was distilled off and the residue was made neutral with 1N HCl and extracted with ethyl acetate. The organic phase was washed with water and sat. sodium chloride solution, dried over $MgSO_4$, filtered and concentrated. The residue was chromatographed on silica gel with ethyl acetate/hexane 1:2. There was obtained 0.01 g (54%) of [3-(4-aminobenzenesulphonyl)-5-bromophenyl]-methylamine as yellow crystals. MS (ISP): me/e=343, 341 ($C_{13}H_{14}BrN_2O_2S^+$).

EXAMPLE 67

[3-(4-Aminophenylsulphonyl)-5-bromophenyl]-dimethylamine 0.79 g (0.002 mol) of N-[3-bromo-5-(4-nitrophenylsulphanyl) -phenyl]-N-methylacetamide was dissolved in a mixture of 10 ml of dioxane and 10 ml of 1N NaOH and heated at reflux for 2 hrs. Subsequently, the organic solvent was distilled off and the residue was made neutral with 1N HCl and extracted with ethyl acetate. The organic phase was washed with water and sat. sodium chloride solution, dried over $MgSO_4$, filtered, concentrated and dried. There was obtained 0.723 g (100%) of [3-bromo-5-(4-nitrophenylsulphanyl)-phenyl]-methylamine as red crystals; m.p.: 96–98° C.

0.34 g (0.001 mol) of [3-bromo-5-(4-nitrophenylsulphanyl)-phenyl]-methylamine was dissolved in 10 ml of acetonitrile, treated with 1.52 ml (0.020 mol) of formaldehyde, 0.74 g (0.010 mol) of $NaBH_3CN$ and 1.76 ml of acetic acid and stirred at room temperature for 1 hr. Thereafter, the solvent was removed, the residue was partitioned in ethyl acetate/water and the organic phase was washed with sat. sodium chloride solution, dried over $MgSO_4$, filtered and concentrated. The residue was chromatographed on silica gel with ethyl acetate/hexane 1:19. There was obtained 0.35 g (99%) of [3-bromo-5-(4-nitrophenylsulphanyl)-phenyl]-dimethylamine as yellow crystals; m.p.: 102–104° C.

0.33 g (0.00093 mol) of [3-bromo-5-(4-nitrophenylsulphanyl) -phenyl]-dimethylamine was dissolved in 35 ml of dichloromethane and treated with 1.1 g (0.0041 mol) of meta-chloroperbenzoic acid (70%). The mixture was stirred at room temperature for 4 hrs. Then, the reaction mixture was extracted with sat. $Na_2CO_3$ solution and with sat. sodium chloride solution. After drying over $MgSO_4$, filtration and removal of the solvent the residue was chromatographed on silica gel with ethyl acetate/hexane 1:9. There was obtained 0.06 g (17%) of [3-bromo-5-(4-nitrobenzenesulphonyl)-phenyl]-dimethylamine as yellow crystals; m.p.: 166–168° C.

0.04 g (0.0001 mol) of [3-bromo-5-(4-nitrobenzenesulphonyl)-phenyl]-dimethylamine was dissolved in a mixture of 5 ml of MeOH and 5 ml of dioxane, treated with 0.04 g of iron powder and a solution of 0.04 g of NH$_4$Cl in 10 ml of water and heated at reflux for 1.5 hrs. Thereafter, the solvents were removed and the residue was treated three times with a 1:1 mixture of MeOH and dichloromethane, with the suspension being suction filtered each time and the filter cake being digested in the solvent mixture. The combined filtrates were concentrated and the residue was chromatographed on silica gel with ethyl acetate/hexane 1:2. There was obtained 0.036 g (97.5%) of 3-(4-amino-phenylsulphonyl)-5-bromophenyl]-dimethylamine as white crystals; m.p.: 205–207 ° C.

EXAMPLE 68

[3-(4-Aminobenzolsulphonyl)-5-bromophenyl]-ethylmethylamine 0.34 g (0.001 mol) of [3-bromo-5-(4-nitrophenylsulphanyl)-phenyl]-methylamine was dissolved in 10 ml of acetonitrile, treated with 1.4 ml (0.025 mol) of acetaldehyde, 0.74 g (0.010 mol) of NaBH$_3$CN and 1.76 ml of acetic acid and stirred at room temperature for 1 hr. Thereafter, the solvent was removed, the residue was partitioned in ethyl acetate/water and the organic phase was washed with sat. sodium chloride solution, dried over MgSO$_4$, filtered and concentrated. The residue was chromatographed on silica gel with ethyl acetate/hexane 1:19. There was obtained 0.33 g (93%) of [3-bromo-5-(4-nitrophenylsulphanyl)-phenyl]-ethylmethylamine as an orange-red oil. MS (EI): me/e=368, 366 (C$_{15}$H$_{15}$BrN$_2$O$_2$S$^+$).

0.33 g (0.00091 mol) of [3-bromo-5-(4-nitrophenylsulphanyl) -phenyl]-ethylmethylamine was dissolved in 35 ml of dichloromethane and treated with 0.49 g (0.002 mol) of meta-chloroperbenzoic acid (70%). The mixture was stirred at room temperature for 2 hrs. Then, the reaction mixture was extracted with sat. Na$_2$CO$_3$ and with sat. sodium chloride solution. After drying over MgSO$_4$, filtration and removal of the solvent there was obtained 0.47 g of a brownish amorphous residue (mixture of sulphone and sulphone N-oxide), which was used directly in the next step.

0.47 g of the amorphous residue from the previous step was dissolved in a mixture of 7 ml of dioxane and 7 ml of methanol, treated with 0.47 g of iron powder and a solution of 0.47 g of NH$_4$Cl in 12 ml of water and boiled at reflux for 1.5 hrs. Thereafter, the solvents were removed and the residue was treated three times with a 1:1 mixture of MeOH and dichloromethane, with the suspension being suction filtered each time and the filter cake being digested in the solvent mixture. The combined filtrates were concentrated and the residue was chromatographed on silica gel with ethyl acetate/hexane 1:4 and subsequently 1:3. There was obtained 0.061 g (18.4%) of [3-(4-amino-phenylsulphonyl)-5-bromophenyl]-ethylmethylamine as orange coloured crystals; m.p.: 162–164° C.

EXAMPLE 69

4-(4-Aminobenzenesulphonyl)-6-bromopyridine-2-carbonitrile 0.44 g (0.002 mol) of 2-bromo-6-methyl-4-nitropyridine was dissolved in 2.2 ml of conc. sulphuric acid, treated with 0.84 g (0.0084 mol) of CrO$_3$ and stirred at room temperature for 18 hrs. Then, the mixture was poured on to ice-water and the precipitate which thereby separated was filtered off under suction, washed with a large amount of water and dried in a high vacuum. There was obtained 0.35 g (70%) of 6-bromo-4-nitro-pyridine-2-carboxylic acid as beige crystals; m.p.: 172–173° C.

1.3 g (0.00526 mol) of 6-bromo-4-nitropyridine-2-carboxylic acid were dissolved in 10 ml of dimethylformamide, treated at 5° C. with 0.94 g (0.0058 mol) of 1,1-carbonyldiimidazole and subsequently stirred at room temperature for 3 hrs. Then, 40 ml of 25% NH$_4$OH in water was added thereto and the mixture was stirred at room temperature for 1 hr. The reaction mixture was partitioned in water and dichloromethane and the organic phase was washed with water and sat. sodium chloride solution, dried over MgSO$_4$ and concentrated. The residue was chromatographed on silica gel with ethyl acetate/hexane 1:1. There were obtained 1.1 g (85%) of 6-bromo-4-nitropyridine-2-carboxamide as white crystals; m.p.: 179–180° C.

0.25 g (0.001 mol) of 6-bromo-4-nitropyridine-2-carboxamide was dissolved in 5 ml of dimethylformamide, treated with 0.19 g (0.001 mol) of 4-nitrothiophenol potassium salt and stirred at room temperature for 18 hrs. The reaction mixture was partitioned in water and ethyl acetate and the organic phase was washed with water and sat. sodium chloride solution, dried over MgSO$_4$ and concentrated in a vaccum. The residue was chromatographed on silica gel with ethyl acetate/hexane 1:1. There was obtained 0.31 g (86%) of 6-bromo-4-(4-nitrophenylsulphanyl)-pyridine-2-carboxamide as yellowish crystals; m.p.: 192–194° C. (dec.).

0.28 g (0.0008 mol) of 6-bromo-4-(4-nitrophenylsulphanyl) -pyridine-2-carboxamide was dissolved in 35 ml of dichloromethane and treated with 1.3 g (0.0053 mol) of meta-chloroperbenzoic acid (70%). The mixture was stirred at room temperature for 2 hrs. Then, it was taken up in sat. Na$_2$CO$_3$ solution and the organic phase was washed with water and sat. sodium chloride solution, dried over MgSO$_4$, filtered and the filtrate was concentrated. The residue was chromatographed on silica gel with ethyl acetate/hexane 1:1. There was obtained 0.29 g (94%) of 6-bromo-4-(4-nitrobenzenesulphonyl)-pyridine-2-carboxamide as white crystals; m.p.: 246–248° C. (dec.).

1.76 g (0.0044 mol) of 6-bromo-4-(4-nitrobenzenesulphonyl)-pyridine-2-carboxamide were suspended in 11 ml of dioxane/THF 1:1, treated with 1.34 ml (0.0096 mol) of triethylamine and cooled to 0° C. 0.69 ml (0.00496 mol) of trifluoroacetic anhydride was slowly added dropwise to this suspension and the mixture was left to warm to room temperature and stirred for 1 hr. The reaction mixture was partitioned in ethyl acetate and water and the organic phase was washed with water and sat. sodium chloride solution, dried over MgSO$_4$, filtered and the filtrate was concentrated. The residue was chromatographed on silica gel with ethyl acetate/hexane 1:4. There were obtained 1.40 g (87%) of 6-bromo-4-(4-nitrobenzenesulphonyl)-pyridine-2-carbonitrile as yellowish crystals; m.p.: 158–160° C.

0.184 g (0.0005 mol) of 6-bromo-4-(4-nitrobenzenesulphonyl)-pyridine-2-carbonitrile was dissolved in 10 ml of methanol/dioxane, treated with 0.37 g of iron powder and a solution of 0.37 g of NH$_4$Cl in 10 ml of water and boiled at reflux for 2 hrs. Then, the reaction mixture was filtered and the filter cake was rinsed with methanol and ethyl acetate. The filtrate was concentrated and the residue was dissolved in ethyl acetate, washed with sat. NaHCO$_3$ solution, water and sat. sodium chloride solution, dried over MgSO$_4$, filtered and concentrated. The residue was chromatographed on silica gel with ethyl acetate/hexane 1:4. There was obtained 0.13 g (75%) of 4-(4-aminobenzenesulphonyl)-6-bromopyridine-2-carbonitrile as yellow crystals; m.p.: 186–188° C.

The invention is further illustrated in the following example.

| Tablet Formulation (Wet Granulation) | | | | |
|---|---|---|---|---|
| Item | Ingredients | | mg/tablet | |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

We claim:
1. Compounds of the formula I:

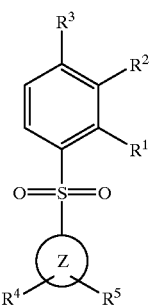

I wherein
$R^1$ is hydrogen;
R is hydrogen, trifluoromethyl or lower alkyl;
$R^3$ is hydrogen or amino; or
$R^1$ and $R^2$ or $R^3$ and $R^2$ taken together are —CH=CH—CH=CH—;
Z is pyrimidin-4-yl, pyridin-4-yl, pyridin-2-yl or phenyl;
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, –N(CH$_3$)(CH$_2$)$_n$NR$^6$R$^7$, —NH(CH$_2$)$_n$-morpholin-4-yl or —NH(CH$_2$)$_n$OH;
n is 2, 3 or 4; and
$R^6$ and $R^7$ are each independently hydrogen or lower alkyl;
and their pharmaceutically acceptable salts,
providing however, that
when Z is pyrimidin-4-yl, $R^4$ is different from $R^5$,
when Z is pyridin-2-yl, $R^5$ is not lower alkyl and
when Z is phenyl, $R^4$ and one of $R^1$–$R^3$ are different from hydrogen.

2. A compound as claimed in claim 1 of formula I-a:

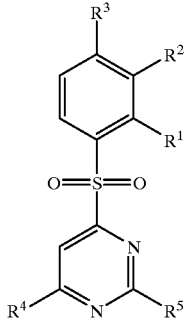

I-a wherein
$R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—; and
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$ NR$^6$R$^7$, —NH(CH$_2$)$_n$-morpholin-4-yl or —NH (CH$_2$)$_n$ OH;
n is 2, 3 or 4;
providing however that $R^4$ is different from $R^5$.

3. A compound according to claim 2 which is [4-(4-aminobenzenesulphonyl)-6-bromopyrimidine-2-yl]-methylamine.

4. A compound as claimed in claim 1 of formula I-b:

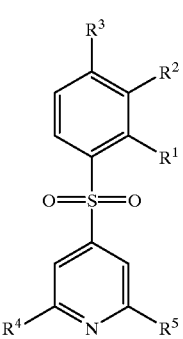

I-b wherein
$R^1$ is hydrogen;
$R^2$ is hydrogen, trifluoromethyl or lower alkyl;
$R^3$ is hydrogen or amino; or
$R^1$ and $R^2$ or $R^3$ and $R^2$ taken together are —CH=CH—CH=CH—; and
$R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH$(CH_2)_n$NR$^6$R$^7$, —N(CH$_3$)(CH$_2)_n$ NR$^6$R$^7$, —NH(CH$_2)_n$-morpholin-4-yl or —NH(CH$_2)_n$ OH;

n is 2, 3 or 4.

5. A compound according to claim 4 which is [4-(4-amino-benzenesulphonyl)-6-bromopyridine-2-yl]-methylamine.

6. A compound according to claim 4 which is [4-(4-amino-benzenesulphonyl)-6-bromopyridine-2-yl]-dimethylamine.

7. A compound according to claim 4 which is 4-(2-chloro-6-pyrrolidine-1-yl-pyridine-4-sulfonyl)-phenylamine.

8. A compound according to claim 4 which is 4-(2-bromo-6-pyrrolidine-1-yl-pyridine-4-sulphonyl)-phenylamine.

9. A compound according to claim 4 which is 4-(2-iodo-6-pyrrolidine-1-yl-pyridine-4-sulphonyl)-phenylamine.

10. A compound according to claim 4 which is 4-(2-bromo-6-piperazin-1-yl-pyridine-4-sulphonyl)-phenylamine.

11. A compound according to claim 4 which is 4-(2-phenyl-6-pyrrolidine-1-yl-pyridine-4-sulphonyl)-phenylamine.

12. A compound according to claim 4 which is N-[4-(4-amino-benzenesulfonyl)-6-bromopyridine-2-yl]-N',N'-dimethylethan-1,2-diamine.

13. A compound according to claim 4 which is N-[4-(4-amino benzenesulphonyl)-6-bromopyridine-2-yl]-N,N',N'-trimethylethan1,2-diamine.

14. A compound according to claim 4 which is N-[4-(4-amino-benzenesulphonyl)-6-bromopyridine-2-yl]-N',N'-dimethylpropane1,3-diamine.

15. A compound according to claim 4 which is N-[4-(4-amino-benzenesulphonyl)-6-bromopyridine-2-yl]-N',N'-diethylpropane-1,3diamine.

16. A compound according to claim 4 which is N1-[4-(4-amino-benzenesulphonyl)-6-bromopyridine-2-yl]-butan-1,4-diamine.

17. A compound according to claim 4 which is 1-[6-bromo-4-(3-trifluoromethyl-benzenesulphonyl)-pyridine-2-yl]piperazin diamine.

18. A compound as claimed in claim 1 of formula I-c:

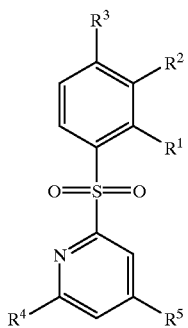

I-c wherein

R$^1$ is hydrogen;
R$^2$ is hydrogen, trifluoromethyl or lower alkyl;
R$^3$ is hydrogen or amino; or
R$^1$ and R$^2$ or R$^3$ and R$^2$ taken together are —CH═CH—CH═CH—; and R$^4$, R$^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH$(CH_2)_n$NR$^6$R$^7$, —N(CH$_3$)(CH$_2)_n$ NR$^6$R$^7$, —NH(CH$_2)_n$-morpholin-4-yl or —NH(CH$_2)_n$ OH;

n is 2, 3 or 4;

providing however that R$^5$ is not lower alkyl.

19. A compound according to claim 18 which is [2-(4-aminobenzenesulphonyl)-6-bromopyridin-4-yl]-methylamine.

20. A compound as claimed in claim 1 of formula I-d:

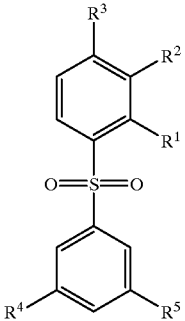

I-d wherein

R$^1$ is hydrogen;
R$^2$ is hydrogen, trifluoromethyl or lower alkyl;
R$^3$ is hydrogen or amino; or
R$^1$ and R$^2$ or R$^3$ and R$^2$ taken together are —CH═CH—CH═CH—; and R$^4$, R$^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH$(CH_2)_n$NR$^6$R$^7$, —N(CH$_3$)(CH$_2)_n$ NR$^6$R$^7$, —NH(CH$_2)_n$-morpholin-4-yl or —NH(CH$_2)_n$ OH;

n is 2, 3 or 4;

providing however that R$^4$ and one of R$^1$–R$^3$ are different from hydrogen.

21. A compound according to claim 20 which is 4-(3,5-dimethoxy-benzenesulphonyl)-phenylamine.

22. A compound according to claim 20 which is [3-(4-amino-benzenesulphonyl)-5-bromophenyl]-methylamine.

23. A compound according to claim 20 which is [3-(4-amino-phenylsulphonyl)-5-bromophenyl]-dimethylamine.

24. A compound according to claim 20 which is [3-(4-amino-benzenesulphonyl)-5-bromophenyl]-ethylmethylamine.

25. A compound according to claim 20 which is 4-[3,5-dimethoxybenzenesulphonyl)-2-methylphenylamine.

26. A compound according to claim 20 which is N-[3-(4-amino-benzenesulphonyl)-5-bromophenyl]-N'-methylpropane-1,3-diamine.

27. A compound according to claim 20 which is 3-[3-(4-amino-benzenesulphonyl)-5-bromophenylamino]-propan-1-ol.

28. A pharmaceutical composition comprising a therepeutically effective amount of a compound of the formula I:

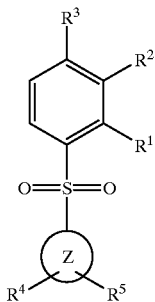

wherein
  $R^1$ is hydrogen;
  $R^2$ is hydrogen, trifluoromethyl or lower alkyl;
  $R^3$ is hydrogen or amino; or
  $R^1$ and $R^2$ or $R^3$ and $R^2$ taken together are —CH=CH—CH=CH—;
  Z is pyrimidin-4-yl, pyridin-4-yl, pyridin-2-yl or phenyl;
  $R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$ NR$^6$R$^7$, —NH(CH$_2$)$_n$-morpholin-4-yl or —NH(CH$_2$)$_n$ OH;
  n is 2, 3 or 4; and
  $R^6$ and $R^7$ are each independently hydrogen or lower alkyl;
providing however, that
  when Z is pyrimidin-4-yl, $R^4$ is different from $R^5$;
  when Z is pyridin-2-yl, $R^5$ is not lower alkyl; and
  when Z is phenyl, $R^4$ and one of $R^1$–$R^3$ are different from hydrogen;
as well as pharmaceutically acceptable salts of said compounds, and a pharmaceutically acceptable carrier.

29. A method of treating phychoses, schizophrenia, manic depressions, depressions, neurological disorders, memory disorders, Parkinson's disease, amyotrophic lateral sclerosis, Alzheimer's disease or Huntington's disease in a host comprising administering to said host a compound of the formula I:

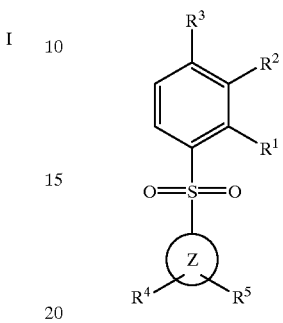

wherein
  $R^1$ is hydrogen;
  $R^2$ is hydrogen, trifluoromethyl or lower alkyl;
  $R^3$ is hydrogen or amino; or
  $R^1$ and $R^2$ or $R^3$ and $R^2$ taken together are —CH=CH—CH=CH—;
  Z is pyrimidin-4-yl, pyridin-4-yl, pyridin-2-yl or phenyl;
  $R^4$, $R^5$ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-buthylethinyl, hydroxyalkylethinyl, phenylethinyl, naphthyl, thiophenyl, or phenyl, which may be substituted by halogen, lower alkoxy, lower alkyl, trifluoromethyl or nitro, or a group —NH(CH$_2$)$_n$NR$^6$R$^7$, —N(CH$_3$)(CH$_2$)$_n$ NR$^6$R$^7$, —NH(CH$_2$)$_n$-morpholin-4-yl or —NH(CH$_2$)$_n$ OH;
  n is 2, 3 or 4; and
  $R^6$ and $R^7$ are each independently hydrogen or lower alkyl,
as well as pharmaceutically acceptable salts of said compunds of formula I in an amount effective for the treatment or prevention of phychoses, schizophrenia, manic depressions, depressions, neurological disorders, memory disorders, Parkinson's disease, amyotrophic lateral sclerosis, Alzheimer's disease or Huntington's disease.

* * * * *

UNITED STATES PATENT AND TRADEMARK OFFICE
CERTIFICATE OF CORRECTION

PATENT NO. : 5,990,105
DATED : November 23, 1999
INVENTOR(S) : Michael Bös et al.

It is certified that error appears in the above-identified patent and that said Letters Patent is hereby corrected as shown below:

In claim 1, column 47, line 45, delete "Ris" and insert therefor

-- $R^2$ is --.

In claim 15, column 49, line 40, delete "1,3diamine" and insert therefor

-- 1,3-diamine --.

Signed and Sealed this

Second Day of May, 2000

Attest:

Q. TODD DICKINSON

*Attesting Officer*  *Director of Patents and Trademarks*